(12) United States Patent
Ackermann et al.

(10) Patent No.: US 7,235,572 B2
(45) Date of Patent: Jun. 26, 2007

(54) THIAZOLYL-INDOLE DERIVATIVES, THEIR MANUFACTURE AND USE AS PHARMACEUTICAL AGENTS

(75) Inventors: Jean Ackermann, Riehen (CH); Johannes Aebi, Basel (CH); Alfred Binggeli, Binningen (CH); Uwe Grether, Loerrach (DE); Georges Hirth, Colmar (FR); Bernd Kuhn, Riehen (CH); Hans-Peter Maerki, Basel (CH); Markus Meyer, Neuenburg (DE); Peter Mohr, Basel (CH); Matthew Blake Wright, Basel (CH)

(73) Assignee: Hoffman-La Roche Inc., Nutley, NJ (US)

( * ) Notice: Subject to any disclaimer, the term of this patent is extended or adjusted under 35 U.S.C. 154(b) by 451 days.

(21) Appl. No.: 10/878,473

(22) Filed: Jun. 28, 2004

(65) Prior Publication Data

US 2005/0004187 A1      Jan. 6, 2005

(30) Foreign Application Priority Data

Jul. 2, 2003   (EP) .................................. 03014476
Jan. 20, 2004  (EP) .................................. 04100157

(51) Int. Cl.
*A61K 31/427*   (2006.01)
*C07D 417/12*   (2006.01)

(52) U.S. Cl. ...................... 514/365; 548/146; 548/181
(58) Field of Classification Search ................ 548/146, 548/181; 514/365
See application file for complete search history.

(56) References Cited

U.S. PATENT DOCUMENTS 6,995,263 B2 *   2/2006   Ackermann et al. ......... 544/333

FOREIGN PATENT DOCUMENTS

EP      207453 A2      1/1987
EP      1 405 848 A1   4/2004
WO      WO 97/31907 A1     9/1997
WO      WO 01/79202 A1    10/2001
WO      WO 02/28433        4/2002
WO      WO 02/30895 A1     4/2002
WO      WO 02/062774 A1    8/2002
WO      WO 03/074051       9/2003
WO      WO 02/102780 A1    4/2004
WO      WO 2004/063190 A1  7/2004

* cited by examiner

*Primary Examiner*—Golam M. M. Shameem
(74) *Attorney, Agent, or Firm*—George W. Johnston; Dennis P. Tramaloni; Brian C. Remy

(57) ABSTRACT

This invention relates to compounds of the formula

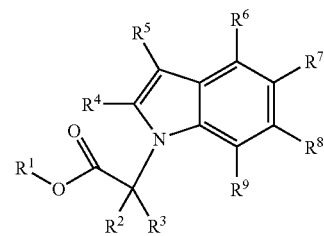

wherein one of $R^6$, $R^7$ or $R^8$ is

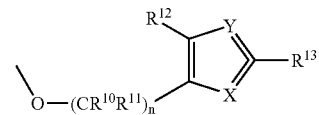

and all enantiomers and pharmaceutically acceptable salts and/or esters thereof as well as pharmaceutical compositions containing such compounds, to a process for their preparation and to their use for the treatment and/or prevention of diseases which are modulated by PPARδ and/or PPARα agonists.

29 Claims, No Drawings

THIAZOLYL-INDOLE DERIVATIVES, THEIR MANUFACTURE AND USE AS PHARMACEUTICAL AGENTS

BACKGROUND OF THE INVENTION

The present invention relates to thiazolyl-indole derivatives and enantiomers and pharmaceutically acceptable salts and esters thereof. The invention also relates to processes for the manufacturing of these compounds, to pharmaceutical compositions containing these compounds and to their use in the manufacture of drugs for the treatment of diseases such as, diabetes and dyslipidemia.

It has been found that compounds of formula I are useful as lipid modulators and insulin sensitizers. In particular, compounds of formula I are PPAR activators.

Peroxisome Proliferator Activated Receptors (PPARs) are members of the nuclear hormone receptor superfamily. The PPARs are ligand-activated transcription factors that regulate gene expression and control multiple metabolic pathways. Three subtypes have been described which are PPARα, PPARδ (also known as PPARβ), and PPARγ. PPARδ is ubiquitously expressed. PPARα is predominantly expressed in the liver, kidney and heart. There are at least two major isoforms of PPARγ. PPARγ1 is expressed in most tissues, and the longer isoform, PPARγ2 is almost exclusively expressed in adipose tissue. The PPARs modulate a variety of physiological responses including regulation of glucose-and lipid-homeostasis and metabolism, energy balance, cell differentiation, inflammation and cardiovascular events.

Approximately half of all patients with coronary artery disease have low concentrations of plasma HDL cholesterol. The atheroprotective function of HDL was first highlighted almost 25 years ago and stimulated exploration of the genetic and environmental factors that influence HDL levels. The protective function of HDL comes from its role in a process termed reverse cholesterol transport. HDL mediates the removal of cholesterol from cells in peripheral tissues including those in the atherosclerotic lesions of the arterial wall. HDL then delivers its cholesterol to the liver and sterol-metabolizing organs for conversion to bile and elimination. Data from the Framingham study showed that HDL-C levels are predictive of coronary artery disease risk independently of LDL-C levels. The estimated age-adjusted prevalence among Americans age 20 and older who have HDL-C of less than 35 mg/dl is 16% (males) and 5.7% (females). A substantial increase of HDL-C is currently achieved by treatment with niacin in various formulations. However, the substantial side-effects limit the therapeutic potential of this approach.

As many as 90% of the 14 million diagnosed type 2 diabetic patients in the US are overweight or obese, and a high proportion of type 2 diabetic patients have abnormal concentrations of lipoproteins. The prevalence of total cholesterol>240 mg/dl is 37% in diabetic men and 44% in women. The respective rates for LDL-C>160 mg/dl are 31% and 44%, respectively, and for HDL-C<35 mg/dl 28% and 11%, respectively. Diabetes is a disease in which a patient's ability to control glucose levels in blood is decreased because of partial impairment in response to the action of insulin. Type II diabetes (T2D) is also called non-insulin dependent diabetes mellitus (NIDDM) and afflicts 80–90% of all diabetic patients in developed countries. In T2D, the pancreatic Islets of Langerhans continue to produce insulin. However, the target organs for insulin action, mainly muscle, liver and adipose tissue, exhibit a profound resistance to insulin stimulation. The body continues to compensate by producing unphysiologically high levels of insulin, which ultimately decreases in later stage of disease, due to exhaustion and failure of pancreatic insulin-producing capacity. Thus T2D is a cardiovascular-metabolic syndrome associated with multiple comorbidities including insulin resistance, dyslipidemia, hypertension, endothelial dysfunction and inflammatory atherosclerosis.

First line treatment for dyslipidemia and diabetes generally involves a low-fat and low-glucose diet, exercise and weight loss. However, compliance can be moderate, and as the disease progresses, treatment of the various metabolic deficiencies becomes necessary with e.g. lipid-modulating agents such as statins and fibrates for dyslipidemia and hypoglycemic drugs, e.g. sulfonylureas or metformin for insulin resistance. A promising new class of drugs has recently been introduced that resensitizes patients to their own insulin (insulin sensitizers), thereby restoring blood glucose and triglyceride levels to normal, and in many cases, obviating or reducing the requirement for exogenous insulin. Pioglitazone (Actos™) and rosiglitazone (Avandia™) belong to the thiazolidinedione (TZD) class of PPARγ-agonists and were the first in their class to be approved for NIDDM in several countries. These compounds, however, suffer from side effects, including rare but severe liver toxicity (as seen with troglitazone). They also increase body weight in patients. Therefore, new, more efficacious drugs with greater safety and lower side effects are urgently needed. Recent studies provide evidence that agonism of PPARδ would result in compounds with enhanced therapeutic potential, i.e. such compounds should improve the lipid profile, with a superior effect on HDL-C raising compared to current treatments and with additional positive effects on normalization of insulin-levels (Oliver et al; Proc Nat Acad Sci USA 2001; 98: 5306–11). Recent observations also suggest that there is an independent PPARα mediated effect on insulin-sensitization in addition to its well known role in reducing triglycerides (Guerre-Millo et al; J Biol Chem 2000; 275: 16638–16642). Thus selective PPARδ agonists or PPARδ agonists with additional PPARα activity may show superior therapeutic efficacy without the side-effects such as the weight gain seen with PPARγ agonists.

The novel compounds of the present invention exceed the compounds known in the art, inasmuch as they bind to and selectively activate PPARδ or coactivate PPARδ and PPARα simultaneously and very efficiently, and with much improved pharmacokinetic properties. Therefore, these compounds combine the anti-dyslipidemic and anti-glycemic effects of PPARδ and PPARα activation with no effect on PPARγ. Consequently, HDL cholesterol is increased, triglycerides lowered (=improved lipid profile) and plasma glucose and insulin are reduced (=insulin sensitization). In addition, such compounds may also lower LDL cholesterol, decrease blood pressure and counteract inflammatory atherosclerosis. Furthermore, such compounds may also be useful for treating inflammatory diseases such as rheumatoid arthritis, osteoarthritis, and psoriasis. Since multiple facets of combined dyslipidemia and the T2D disease syndrome are addressed by PPARδ-selective agonists and PPARδ and α coagonists, they are expected to have an enhanced therapeutic potential compared to the compounds already known in the art.

Compounds modulating PPAR activity are known inter alia from International Patent Application No. WO 03/074051, published on 12 Sep. 2003. The compound having the formula

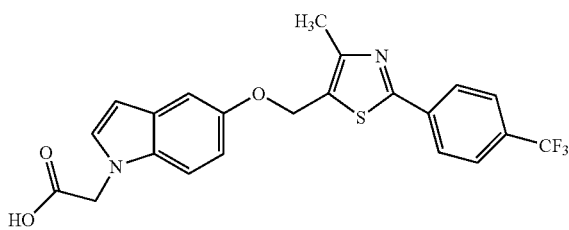

is specifically described therein.

The compounds of the present invention further exhibit improved pharmacological properties compared to known compounds.

SUMMARY OF THE INVENTION

The present invention is concerned with novel thiazolyl-indolyl derivatives of the formula

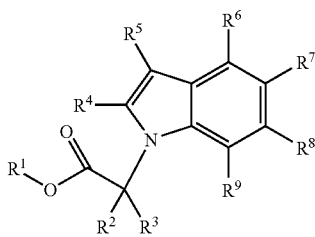

I and enantiomers and pharmaceutically acceptable salts and esters thereof, wherein $R^1$, $R^2$, $R^3$, $R^4$, $R^5$, $R^6$, $R^7$, $R^8$ and $R^9$ are as described herewithin.

DETAILED DESCRIPTION OF THE INVENTION

The present invention is concerned with novel indolyl derivatives of the formula

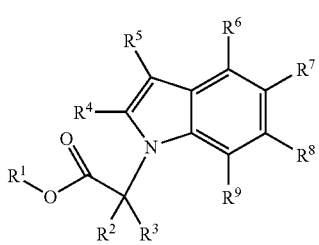

I and enantiomers and pharmaceutically acceptable salts and esters thereof, wherein $R^1$ is hydrogen or $C_{1-7}$-alkyl;

$R^2$ and $R^3$ independently from each other are hydrogen, $C_{1-7}$-alkyl or $C_{1-7}$-alkoxy;

$R^4$ and $R^5$ independently from each other are hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano;

$R^6$, $R^7$, $R^8$ and $R^9$ independently from each other are hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano;

and one of $R^6$, $R^7$ and $R^8$ is

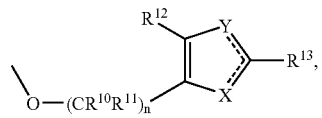

wherein

X is N and Y is S; or

X is S and Y is N;

$R^{10}$ is hydrogen, $C_{1-7}$-alkyl, $C_{3-7}$-cycloalkyl or fluoro-$C_{1-7}$-alkyl;

$R^{11}$ is hydrogen, $C_{1-7}$-alkyl or $C_{1-7}$-alkoxy-$C_{1-7}$-alkyl;

$R^{12}$ is hydrogen, $C_{1-7}$-alkyl, $C_{3-7}$-cycloalkyl or fluoro-$C_{1-7}$-alkyl;

$R^{13}$ is aryl or heteroaryl; and n is 1, 2 or 3.

Unless otherwise indicated the following definitions are set forth to illustrate and define the meaning and scope of the various terms used to describe the invention herein.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_{1-7}$-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the groups specifically exemplified herein.

The term "halogen" refers to fluorine, chlorine, bromine and iodine.

The term "fluoro-lower alkyl" or "fluoro-$C_{1-7}$-alkyl" refers to lower alkyl groups which are mono-or multiply substituted with fluorine. Examples of fluoro-lower alkyl groups are e.g. —$CF_3$, —$CH_2CF_3$, —$CH(CF_3)_2$ and the groups specifically exemplified herein.

The term "alkoxy" refers to the group R'—O—, wherein R' is alkyl. The term "lower-alkoxy" or "$C_{1-7}$-alkoxy" refers to the group R'—O—, wherein R' is lower-alkyl. Examples of lower-alkoxy groups are e.g. methoxy, ethoxy, propoxy, isopropoxy, butoxy, isobutoxy and hexyloxy. Preferred are the lower-alkoxy groups specifically exemplified herein.

The term "lower alkenyl" or "$C_{2-7}$-alkenyl", alone or in combination, signifies a straight-chain or branched hydrocarbon residue comprising an olefinic bond and up to 7, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl.

The term "lower alkinyl" or "$C_{2-7}$-alkinyl", alone or in combination, signifies a straight-chain or branched hydrocarbon residue comprising a triple bond and up to 7, preferably up to 6, particularly preferred up to 4 carbon atoms. Examples of alkinyl groups are ethinyl, 1-propinyl, or 2-propinyl.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl.

The term "aryl" relates to the phenyl or naphthyl group, preferably the phenyl group, which can optionally be mono- or multiply-substituted, particularly mono- or di-substituted by halogen, hydroxy, CN, $CF_3$, $NO_2$, $NH_2$, N(H, lower-alkyl), N(lower-alkyl)$_2$, carboxy, aminocarbonyl, lower-alkyl, lower-alkoxy, aryl and/or aryloxy. Preferred substituents are halogen, $CF_3$, lower-alkyl and/or lower-alkoxy. Preferred are the specifically exemplified aryl groups.

The term "heteroaryl" refers to an aromatic 5- or 6-membered ring which can comprise 1, 2 or 3 atoms selected from nitrogen, oxygen and/or sulphur such as furyl, pyridyl, 1,2-, 1,3-and 1,4-diazinyl, thienyl, isoxazolyl, oxazolyl, imidazolyl, or pyrrolyl. The term "heteroaryl" further refers to bicyclic aromatic groups comprising two 5- or 6-membered rings, in which one or both rings can contain 1, 2 or 3 atoms selected from nitrogen, oxygen or sulphur such as e.g. indole or quinoline, or partially hydrogenated bicyclic aromatic groups such as e.g. indolinyl. A heteroaryl group may have a substitution pattern as described earlier in connection with the term "aryl". Preferred heteroaryl groups are e.g. thienyl and furyl which can optionally be substituted as described above, preferably with halogen, $CF_3$, lower-alkyl and/or lower-alkoxy.

The term "protecting group" refers to groups such as e.g. acyl, alkoxycarbonyl, aryloxycarbonyl, silyl, or imine-derivatives, which are used to temporarily block the reactivity of functional groups. Well known protecting groups are e.g. t-butyloxycarbonyl, benzyloxycarbonyl, fluorenylmethyloxycarbonyl or diphenylmethylene which can be used for the protection of amino groups, or lower-alkyl-, β-trimethylsilylethyl- and β-trichloroethyl-esters, which can be used for the protection of carboxy groups.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

The term "pharmaceutically acceptable salts" embraces salts of the compounds of formula (I) with pharmaceutically acceptable bases such as alkali salts, e.g. Na- and K-salts, alkaline earth salts, e.g. Ca- and Mg-salts, and ammonium or substituted ammonium salts, such as e.g. trimethylammonium salts. The term "pharmaceutically acceptable salts" also relates to such salts.

The compounds of formula (I) can also be solvated, e.g. hydrated. The solvation can be effected in the course of the manufacturing process or can take place e.g. as a consequence of hygroscopic properties of an initially anhydrous compound of formula (I) (hydration).

The term pharmaceutically acceptable salts also includes pharmaceutically acceptable solvates.

The term "pharmaceutically acceptable esters" embraces derivatives of the compounds of formula (I), in which a carboxy group has been converted to an ester. Lower-alkyl, hydroxy-lower-alkyl, lower-alkoxy-lower-alkyl, amino-lower-allyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. The methyl, ethyl, propyl, butyl and benzyl esters are preferred esters. The methyl and ethyl esters are especially preferred. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

More specifically, the present invention relates to compounds of the formula

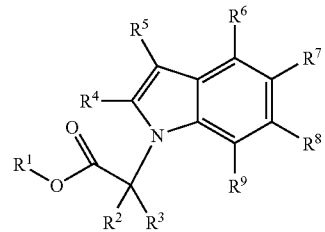

I wherein $R^1$ is hydrogen or $C_{1-7}$-alkyl;

$R^2$ and $R^3$ independently from each other are hydrogen, $C_{1-7}$-alkyl or $C_{1-7}$-alkoxy;

$R^4$ and $R^5$ independently from each other are hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano;

$R^6$, $R^7$, $R^8$ and $R^9$ independently from each other are hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano;

and one of $R^6$, $R^7$ and $R^8$ is

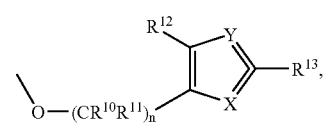

wherein

X is N and Y is S; or

X is S and Y is N;

$R^{10}$ is hydrogen, $C_{1-7}$-alkyl, $C_{3-7}$-cycloalkyl or fluoro-$C_{1-7}$-alkyl;

$R^{11}$ is hydrogen, $C_{1-7}$-alkyl or $C_{1-7}$-alkoxy-$C_{1-7}$-alkyl;

$R^{12}$ is hydrogen, $C_{1-7}$-alkyl, $C_{3-7}$-cycloalkyl or fluoro-$C_{1-7}$-alkyl;

$R^{13}$ is aryl or heteroaryl;

n is 1, 2 or 3; and all enantiomers and pharmaceutically acceptable salts and/or esters thereof, provided that compounds of formula I are excluded, wherein one of $R^7$ or $R^8$ is

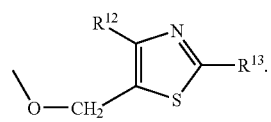

Preferably, the present invention relates to compounds of the formula (I)

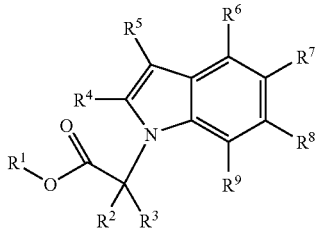

I wherein
R$^1$ is hydrogen or C$_{1-7}$-alkyl;
R$^2$ and R$^3$ independently from each other are hydrogen, C$_{1-7}$-alkyl or C$_{1-7}$-alkoxy;
R$^4$ and R$^5$ independently from each other are hydrogen, C$_{1-7}$-alkyl, C$_{3-7}$-cycloalkyl, halogen, C$_{1-7}$-alkoxy-C$_{1-7}$-alkyl, C$_{2-7}$-alkenyl, C$_{2-7}$-alkinyl, fluoro-C$_{1-7}$-alkyl, cyano-C$_{1-7}$-alkyl or cyano;
R$^6$, R$^7$, R$^8$ and R$^9$ independently from each other are hydrogen, C$_{1-7}$-alkyl, C$_{3-7}$-cycloalkyl, halogen, C$_{1-7}$-alkoxy-C$_{1-7}$-alkyl, C$_{2-7}$-alkenyl, C$_{2-7}$-alkinyl, fluoro-C$_{1-7}$-alkyl, cyano-C$_{1-7}$-alkyl or cyano;
and one of R$^6$, R$^7$ and R$^8$ is

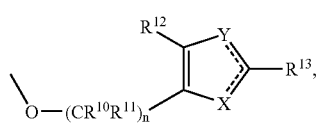

wherein
X is N and Y is S; or
X is S and Y is N;
R$^{10}$ is hydrogen, C$_{1-7}$-alkyl, C$_{3-7}$-cycloalkyl or fluoro-C$_{1-7}$-alkyl;
R$^{11}$ is hydrogen, C$_{1-7}$-alkyl or C$_{1-7}$-alkoxy-C$_{1-7}$-alkyl;
R$^{12}$ is hydrogen, C$_{1-7}$-alkyl, C$_{3-7}$-cycloalkyl or fluoro-C$_{1-7}$-alkyl;
R$^{13}$ is aryl or heteroaryl;
n is 1, 2 or 3; and all enantiomers and pharmaceutically acceptable salts and/or esters thereof, provided that {5-[4-methyl-2-(4-trifluoromethyl-phenyl)-thiazol-5-ylmethoxy]-indol-1-yl}-acetic acid is excluded.

Preferred compounds of formula I of the present invention are compounds of formula

I-A

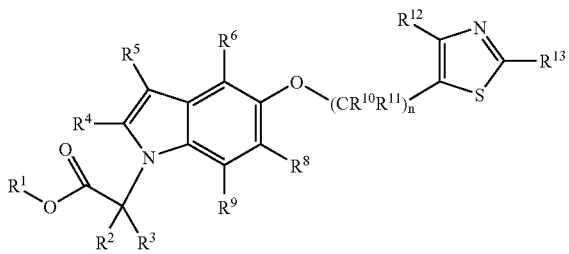

wherein
R$^1$, R$^2$, R$^3$, R$^4$, R$^5$, R$^{10}$, R$^{11}$, R$^{12}$, R$^{13}$ and n are as defined herein before;
R$^6$, R$^7$ and R$^9$ independently from each other are hydrogen, C$_{1-7}$-alkyl, C$_{3-7}$-cycloalkyl, halogen, C$_{1-7}$-alkoxy-C$_{1-7}$-alkyl, C$_{2-7}$-alkenyl, C$_{2-7}$-alkinyl, fluoro-C$_{1-7}$-alkyl, cyano-C$_{1-7}$-alkyl or cyano; and all enantiomers and pharmaceutically acceptable salts and/or esters thereof.

More preferred are those compounds of formula I-A in accordance with the present invention, wherein R$^6$, R$^7$ and R$^9$ are hydrogen.

Also preferred are compounds of formula I having the formula

I-B

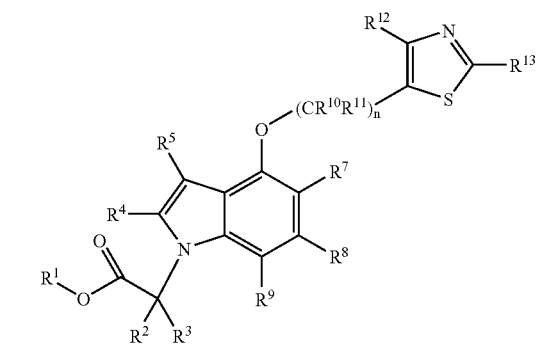

wherein
R$^1$, R$^2$, R$^3$, R$^4$, R$^5$, R$^{10}$, R$^{11}$, R$^{12}$, R$^{13}$ and n are as defined in claim 1;
R$^6$, R$^8$ and R$^9$ independently from each other are hydrogen, C$_{1-7}$-alkyl, C$_{3-7}$-cycloalkyl, halogen, C$_{1-7}$-alkoxy-C$_{1-7}$-alkyl, C$_{2-7}$-alkenyl, C$_{2-7}$-alkinyl, fluoro-C$_{1-7}$-alkyl, cyano-C$_{1-7}$-alkyl or cyano; and all enantiomers and pharmaceutically acceptable salts and/or esters thereof.

Especially preferred are compounds of formula I-B, wherein R$^6$, R$^8$ and R$^9$ are hydrogen.

Further preferred compounds of formula I have the formula

I-C

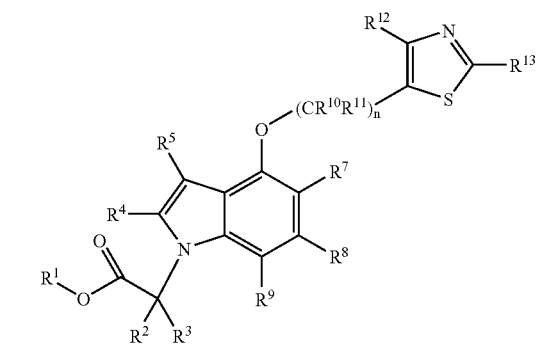

wherein
R$^1$, R$^2$, R$^3$, R$^4$, R$^5$, R$^{10}$, R$^{11}$, R$^{12}$, R$^{13}$ and n are as defined in claim 1;
R$^7$, R$^8$ and R$^9$ independently from each other are hydrogen, C$_{1-7}$-alkyl, C$_{3-7}$-cycloalkyl, halogen, C$_{1-7}$-alkoxy-C$_{1-7}$-alkyl, C$_{2-7}$-alkenyl, C$_{2-7}$-alkinyl, fluoro-C$_{1-7}$-alkyl, cyano-C$_{1-7}$-alkyl or cyano; and all enantiomers and pharmaceutically acceptable salts and/or esters thereof.

More preferred are those compounds of formula I-C, wherein R$^7$, R$^8$ and R$^9$ are hydrogen.

Also preferred are compounds of formula I having the formula

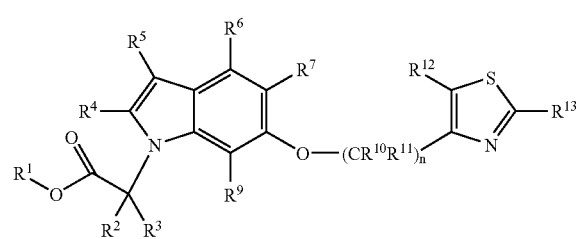

I-D wherein
$R^1$, $R^2$, $R^3$, $R^4$, $R^5$, $R^{10}$, $R^{11}$, $R^{12}$, $R^{13}$ and n are as defined in claim 1;
$R^6$, $R^7$ and $R^9$ independently from each other are hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano; and all enantiomers and pharmaceutically acceptable salts and/or esters thereof.

Especially preferred are those compounds of formula I-A, wherein $R^6$, $R^7$ and $R^9$ are hydrogen.

Furthermore, compounds of formula I, wherein $R^1$ is hydrogen, are preferred. Compounds of formula I, wherein $R^2$ and $R^3$ independently from each other are hydrogen or methyl, are also preferred.

Preferred are further compounds of formula I, wherein $R^4$ is hydrogen.

Compounds of formula I, wherein $R^5$ is hydrogen, $C_{1-7}$-alkyl or halogen, are also preferred.

Other preferred compounds of formula I according to the present invention are those, wherein $R^{10}$ is hydrogen, $C_{1-7}$-alkyl or $C_{3-7}$-cycloalkyl. Especially preferred are compounds of formula I, wherein $R^{10}$ is $C_{1-7}$-alkyl or $C_{3-7}$-cycloalkyl.

Furthermore, compounds of formula I, wherein $R^{11}$ is hydrogen, are preferred.

The integer n is 1, 2 or 3. Preferred are compounds of formula I, wherein n is 1 or 2.

Especially preferred are compounds of formula I, wherein n is 2.

Further preferred compounds of formula I of the present invention are those, wherein $R^{12}$ is hydrogen or $C_{1-7}$-alkyl, with those compounds, wherein $R^{12}$ is methyl, being particularly preferred.

Compounds of formula I, wherein $R^{13}$ is aryl, are preferred. More preferred are those compounds of formula I, wherein $R^{13}$ is unsubstituted phenyl or phenyl substituted with one to three groups selected from $C_{1-7}$-alkyl, $C_{1-7}$-alkoxy, halogen, fluoro-$C_{1-7}$-alkyl and cyano, with those compounds, wherein $R^{13}$ is phenyl substituted with halogen or fluoro-$C_{1-7}$-alkyl, being particularly preferred. Especially preferred are those compounds, wherein $R^{13}$ is 4-trifluoromethylphenyl.

Examples of preferred compounds of formula I are the following:
{4-[4-methyl-2-(4-trifluoromethyl-phenyl)-thiazol-5-ylmethoxy]-indol-1-yl}-acetic acid,
[rac]-(6-{1-[4-methyl-2-(4-trifluoromethyl-phenyl)-thiazol-5-yl]-ethoxy}-indol-1-yl) acetic acid,
[rac]-(4-{2-methyl-1-[4-methyl-2-(4-trifluoromethyl-phenyl)-thiazol-5-yl]-propoxy}-indol-1-yl)-acetic acid,
[rac]-2-{4-[4-methyl-2-(4-trifluoromethyl-phenyl)-thiazol-5-ylmethoxy]-indol-1-yl}-propionic acid,
(4-{2-[4-methyl-2-(4-trifluoromethyl-phenyl)-thiazol-5-yl]-ethoxy}-indol-1-yl)-acetic acid,
{6-[2-(4-trifluoromethyl-phenyl)-thiazol-5-ylmethoxy]-indol-1-yl}-acetic acid,
(6-{2-[4-methyl-2-(4-trifluoromethyl-phenyl)-thiazol-5-yl]-ethoxy}-indol-1-yl)-acetic acid,
(4-{3-[4-methyl-2-(4-trifluoromethyl-phenyl)-thiazol-5-yl]-propoxy}-indol-1-yl)-acetic acid,
[rac]-(6-{2-methyl-1-[4-methyl-2-(4-trifluoromethyl-phenyl)-thiazol-5-yl]-propoxy}-indol-1-yl)-acetic acid,
(6-{3-[4-methyl-2-(4-trifluoromethyl-phenyl)-thiazol-5-yl]-propoxy}-indol-1-yl)-acetic acid,
(S)-(6-{1-[4-methyl-2-(4-trifluoromethyl-phenyl)-thiazol-5-yl]-ethoxy}-indol-1-yl) -acetic acid,
(R)-(6-{1-[4-methyl-2-(4-trifluoromethyl-phenyl)-thiazol-5-yl]-ethoxy}-indol-1-yl) -acetic acid,
[6-(5-methyl-2-phenyl-thiazol-4-ylmethoxy)-indol-1-yl]-acetic acid,
[rac]-(5-{1-[4-methyl-2-(4-trifluoromethyl-phenyl)-thiazol-5-yl]-ethoxy}-indol-1-yl)-acetic acid,
(6-{2-[5-methyl-2-(4-trifluoromethyl-phenyl)-thiazol-4-yl]-ethoxy}-indol-1-yl)-acetic acid,
(6-{2-[2-(4-trifluoromethyl-phenyl)-thiazol-4-yl]-ethoxy}-indol-1-yl)-acetic acid,
(3-chloro-6-{2-[4-methyl-2-(4-trifluoromethyl-phenyl)-thiazol-5-yl]-ethoxy}-indol-1-yl)-acetic acid,
(6-{2-[4-methyl-2-(3-trifluoromethyl-phenyl)-thiazol-5-yl]-ethoxy}-indol-1-yl)-acetic acid,
{6-[2-(4-methyl-2-phenyl-thiazol-5-yl)-ethoxy]-indol-1-yl}-acetic acid,
(3-methyl-6-{2-[4-methyl-2-(4-trifluoromethyl-phenyl)-thiazol-5-yl]-ethoxy}-indol-1-yl)-acetic acid,
(6-{2-[4-methyl-2-(4-trifluoromethyl-phenyl)-thiazol-5-yl]-ethoxy}-3-propyl-indol-1-yl)-acetic acid,
{6-[5-methyl-2-(4-trifluoromethyl-phenyl)-thiazol-4-ylmethoxy]-indol-1-yl}-acetic acid,
(6-{2-[4-methyl-2-(4-trifluoromethoxy-phenyl)-thiazol-5-yl]-ethoxy}-indol-1-yl)-acetic acid,
[rac]-(6-{4-hydroxy-1-[4-methyl-2-(4-trifluoromethyl-phenyl)-thiazol-5-yl]-butoxy}-indol-1-yl)-acetic acid, and
{6-[2-(5-methyl-2-phenyl-thiazol-4-yl)-ethoxy]-indol-1-yl}-acetic acid.

Particularly preferred compounds of formula I of the present invention are the following:
[rac]-(6-{1-[4-methyl-2-(4-trifluoromethyl-phenyl)-thiazol-5-yl]-ethoxy}-indol-1-yl)-acetic acid,
{6-[2-(4-trifluoromethyl-phenyl)-thiazol-5-ylmethoxy]-indol-1-yl}-acetic acid,
(6-{2-[4-methyl-2-(4-trifluoromethyl-phenyl)-thiazol-5-yl]-ethoxy}-indol-1-yl)-acetic acid,
(4-{3-[4-methyl-2-(4-trifluoromethyl-phenyl)-thiazol-5-yl]-propoxy}-indol-1-yl)-acetic acid,
(6-{3-[4-methyl-2-(4-trifluoromethyl-phenyl)-thiazol-5-yl]-propoxy}-indol-1-yl)-acetic acid,
(R)-(6-{1-[4-methyl-2-(4-trifluoromethyl-phenyl)-thiazol-5-yl]-ethoxy}-indol-1-yl) -acetic acid,
[rac]-(5-{1-[4-methyl-2-(4-trifluoromethyl-phenyl)-thiazol-5-yl]-ethoxy}-indol-1-yl)-acetic acid,
(3-chloro-6-{2-[4-methyl-2-(4-trifluoromethyl-phenyl)-thiazol-5-yl]-ethoxy}-indol-1-yl)-acetic acid, and
(6-{2-[4-methyl-2-(4-trifluoromethoxy-phenyl)-thiazol-5-yl]-ethoxy}-indol-1-yl)-acetic acid.

Especially preferred are also the following compounds of formula I of the present invention:
(6-{2-[4-methyl-2-(4-trifluoromethyl-phenyl)-thiazol-5-yl]-ethoxy}-indol-1-yl)-acetic acid,
(6-{3-[4-methyl-2-(4-trifluoromethyl-phenyl)-thiazol-5-yl]-propoxy}-indol-1-yl)-acetic acid,
(R)-(6-{1-[4-methyl-2-(4-trifluoromethyl-phenyl)-thiazol-5-yl]-ethoxy}-indol-1-yl)-acetic acid, and
[rac]-(5-{1-[4-methyl-2-(4-trifluoromethyl-phenyl)-thiazol-5-yl]-ethoxy}-indol-1-yl)-acetic acid.

Furthermore, the pharmaceutically acceptable salts of the compounds of formula I and the pharmaceutically acceptable esters of the compounds of formula I individually constitute preferred embodiments of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbent or eluant). The invention embraces all of these forms.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula (I) as defined above, which process comprises
a) reacting a compound of formula

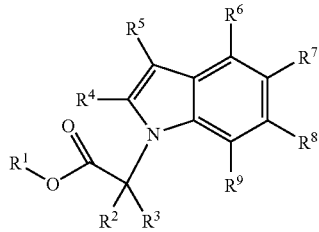

II wherein $R^1$ is $C_{1-7}$-alkyl, $R^2$, $R^3$, $R^4$ and $R^5$ are as defined as in claim 1 and $R^6$, $R^7$, $R^8$ and $R^9$ are selected from hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl, and cyano with the proviso that one of $R^6$, $R^7$ or $R^8$ is —OH,
with a compound of formula

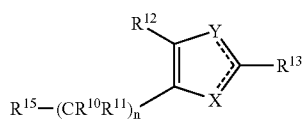

III wherein X, Y, $R^{10}$, $R^{11}$, $R^{12}$, $R^{13}$ and n are as defined in claim 1 and $R^{15}$ is —OH, —Cl, —Br, —I or another leaving group, to obtain a compound of formula

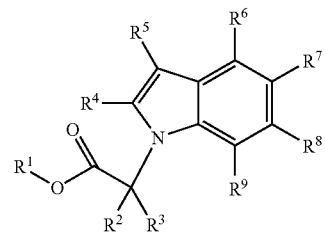

I wherein $R^1$ is $C_{1-7}$-alkyl and $R^2$ to $R^9$ are as defined in claim 1,
and optionally hydrolysing the ester group to obtain a compound of formula I, wherein $R^1$ is hydrogen;
or, alternatively,
b) reacting a compound of formula

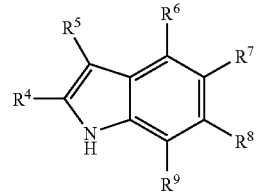

IV wherein $R^4$ to $R^9$ are as defined as in claim 1,
with a compound of formula

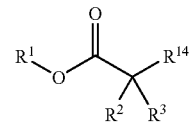

V wherein $R^1$ is $C_{1-7}$-allyl, $R^2$ and $R^3$ are as defined in claim 1 and $R^{14}$ is halogen, triflate or another leaving group, to obtain a compound of formula

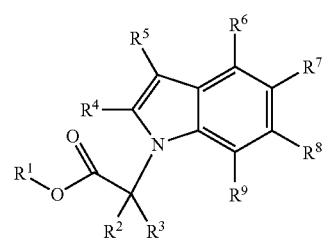

I wherein $R^1$ is $C_{1-7}$-alkyl and $R^2$ to $R^9$ are as defined in claim 1,
and optionally hydrolyzing the ester group to obtain a compound of formula I, wherein $R^1$ is hydrogen.

As described above, the compounds of formula (I) of the present invention can be used as medicaments for the treatment and/or prevention of diseases which are modulated by PPARδ and/or PPARα agonists. Examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), obesity, elevated blood pressure, endothelial dysfunction, procoagulant state, dyslipidemia, polycystic ovary syndrome, inflammatory diseases (such as e.g. Crohn's disease, inflammatory bowel disease, colitis, pancreatitis, cholestasis/fibrosis of the liver, rheumatoid arthritis, osteoarthritis, psoriasis and other skin disorders, and diseases that have an inflammatory component such as e.g. Alzheimer's disease or impaired/improvable cognitive function) and proliferative diseases (cancers such as e.g. liposarcoma, colon cancer, prostate cancer, pancreatic cancer and breast cancer). The use as medicament for the treatment of low HDL cholesterol levels, high LDL cholesterol levels, high triglyceride levels, and the metabolic syndrome (syndrome X) is preferred. Also preferred is the use as medicament for the treatment of obesity.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are modulated by PPARδ and/or PPARα agonists. Examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), elevated blood pressure, endothelial dysfunction, procoagulant state, dyslipidemia, polycystic ovary syndrome, inflammatory diseases such as rheumatoid arthritis, osteoarthritis, psoriasis and other skin disorder, and proliferative diseases.

In another embodiment, the invention relates to a method for the treatment and/or prevention of diseases which are modulated by PPARδ and/or PPARα agonists, which method comprises administering a compound of formula (I) to a human or animal. Preferred examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), elevated blood pressure, endothelial dysfunction, procoagulant state, dyslipidemia, polycystic ovary syndrome, inflammatory diseases such as rheumatoid arthritis, osteoarthritis, psoriasis and other skin disorder, and proliferative diseases.

The invention further relates to the use of compounds as defined above for the treatment and/or prevention of diseases which are modulated by PPARδ and/or PPARα agonists. Preferred examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), elevated blood pressure, endothelial dysfunction, procoagulant state, dyslipidemia, polycystic ovary syndrome, inflammatory diseases such as rheumatoid arthritis, osteoarthritis, psoriasis and other skin disorder, and proliferative diseases.

In addition, the invention relates to the use of compounds as defined above for the preparation of medicaments for the treatment and/or prevention of diseases which are modulated by PPARδ and/or PPARα agonists. Preferred examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), elevated blood pressure, endothelial dysfunction, procoagulant state, dyslipidemia, polycystic ovary syndrome, inflammatory diseases such as rheumatoid arthritis, osteoarthritis, psoriasis and other skin disorder, and proliferative diseases. Such medicaments comprise a compound as defined above.

The compounds of formula (I) can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

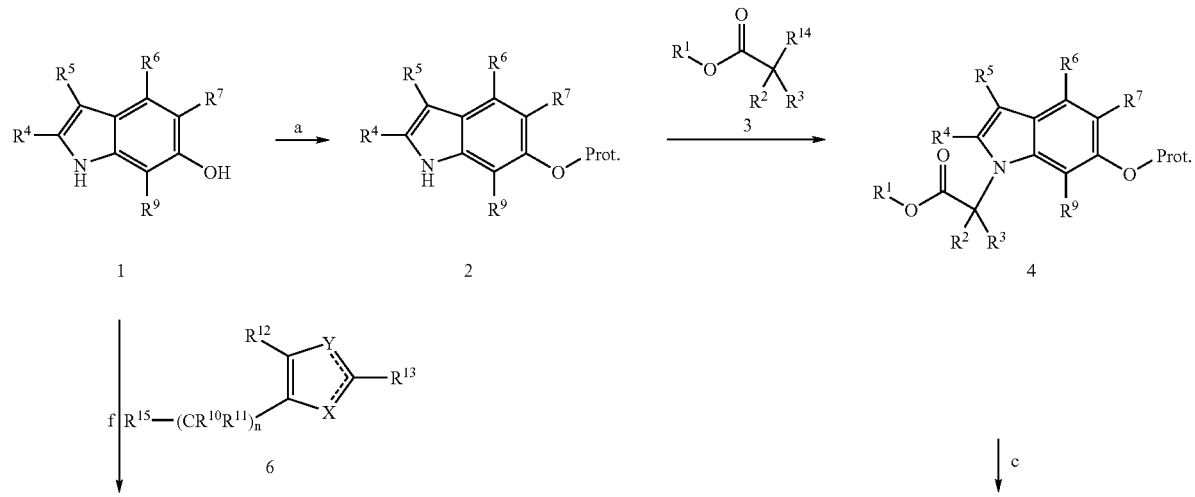

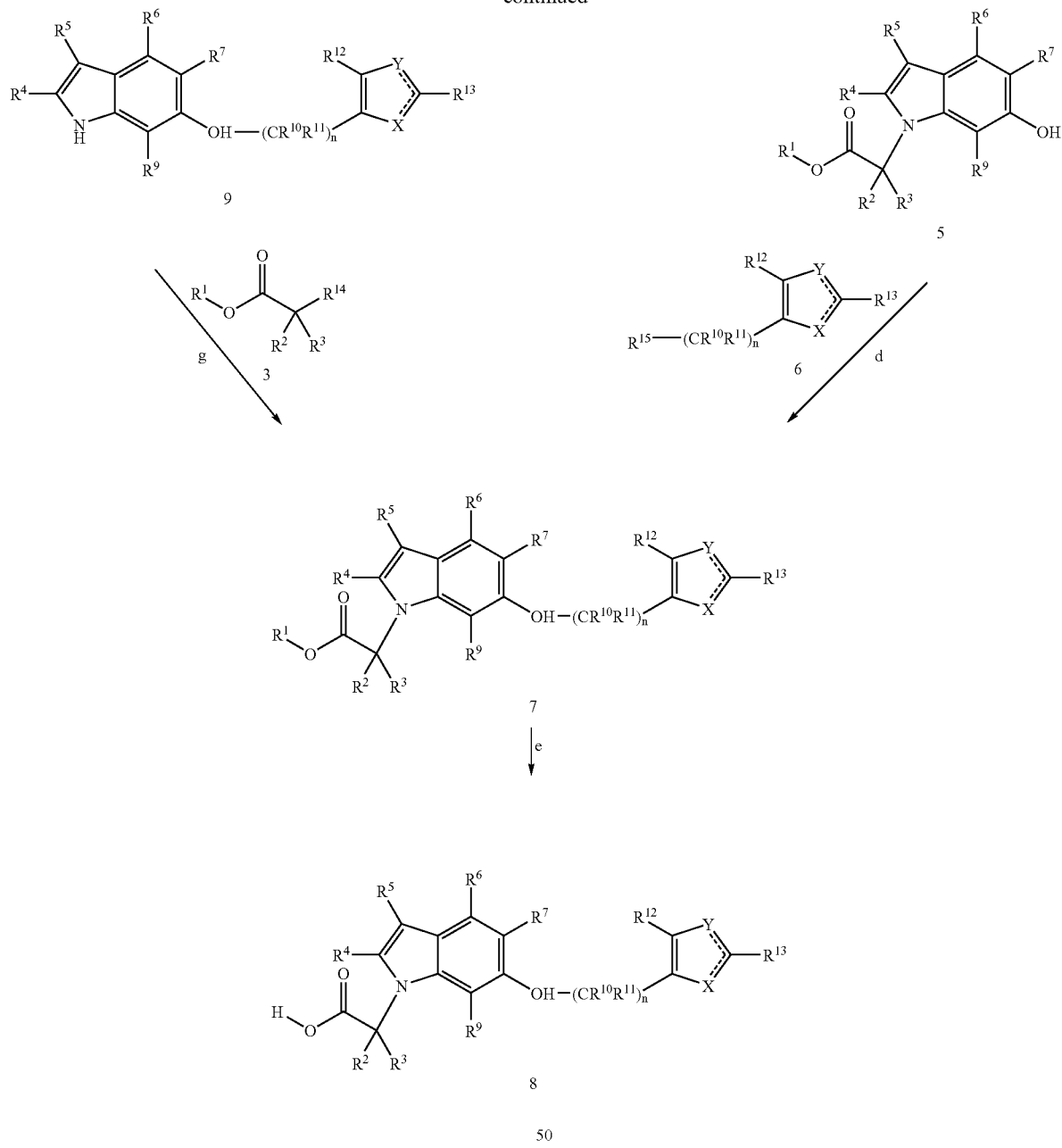

Compounds of formula (I) (compounds 7 and 8 in scheme 1) can be synthesized according to the methods depicted in scheme 1 for $R^8$ being equal to

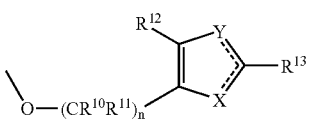

with $R^{10}$, $R^{11}$, $R^{12}$, $R^{13}$ and n having the meanings as defined herein before.

The same reaction sequences can be applied to synthesize compounds of formula (I) where $R^6$ or $R^7$ is equal to 6-Hydroxyindols 1 and the regioisomeric 4- and 5-hydroxyindols are commercially available, known or can be synthesized by methods known in the art. The hydroxy function of compounds 1 can be protected by methods described in the literature, e.g. by treating them with tert-butyldimethylsilyl chloride in the presence of imidazole, preferably at room temperature in solvents like N,N-dimethylformamide, to obtain the corresponding tert-butyldimethylsilyl ethers 2 (step a). N-Alkylation of intermediates 2 with carboxylic acid ester 3, where $R^{14}$ can be equal to e.g. chlorine, bromine, triflate, or another leaving group, delivers indoles 4 and can be performed by standard technology; e.g. in the presence of $K_2CO_3$ or $Cs_2CO_3$ at temperatures between 10° C. and the reflux temperature of the solvent in a solvent like acetonitrile or acetone or in the presence of sodium hydride at temperatures between −10° C. and 50° C. in a solvent like N,N-dimethylformamide (step b). Ester derivatives 3 are commercially available or can be synthesized by methods known in the art. Deprotection of indoles 4 by methods described in the literature, e.g. by treatment with tetrabutyl ammonium fluoride at temperatures between −15° C. and ambient temperature in a solvent like tetrahydrofuran, provided that the protection group is a silyl ether, gives hydroxyindols 5 (step c). Aryl-thiazole compounds 6 (prepared as outlined in schemes 3–6) are condensed with hydroxyindols 5 according to well known procedures: if $R^{15}$ represents a hydroxy group e.g. via Mitsunobu-reaction, with triphenylphosphine and di-tert-butyl-, diisopropyl- or diethyl-azodicarboxylate as reagents, or by using tributylphosphine and N,N,N',N'-tetramethyl azodicarboxamide; this transformation is preferably carried out in a solvent like toluene, dichloromethane or tetrahydrofuran at ambient temperature. Alternatively, if $R^{15}$ represents a halide, mesylate or tosylate moiety, the aryl-thiazole compounds 6 can be reacted with hydroxyindols 5 in solvents like N,N-dimethylformamide, acetonitrile, acetone or methyl-ethyl ketone in the presence of a weak base like cesium or potassium carbonate at a temperature ranging from room temperature to 140° C., preferably around 50° C., to yield ether compounds 7 (step d). Those can optionally be hydrolyzed according to standard procedures, e.g. by treatment with an alkali hydroxide like LiOH or NaOH in a polar solvent mixture like tetrahydrofuran/ethanol/water leading to carboxylic acids 8 (step e). If the aryl-thiazole compounds 6 (prepared as described in schemes 3–6) and/or the hydroxyindols 5 contain chiral centers, ester compounds 7 and carboxylic acids 8 are obtained as mixtures of diastereomers or enantiomers, which can be separated by methods well known in the art, e.g. (chiral) HPLC chromatography or crystallization.

Carboxylic acid esters 7 can alternatively be synthesized via regioselective condensation of aryl-thiazoles 6 with hydroxyindols 1 under the conditions given in step d (step f) and subsequent alkylation of the obtained ethers 9 with alkylating reagents 3 as described for the synthesis of esters 4 in step b (step g).

6-Hydroxyindoles 1 (scheme 1) and O-protected 6-hydroxyindols 2 (scheme 1) as well as their regioisomeric 4- and 5-hydroxyindol analogues are known or can be synthesized by methods known in the art. Examples for possible syntheses of these key intermediates (compounds 6 and 7 in scheme 2) are given in scheme 2 for $R^8$ in I being equal to hydroxy or protected hydroxy. Analogous key intermediates where $R^6$ or $R^7$ is equal to hydroxy or hydroxy carrying a protecting group can be synthesized applying the same reaction sequence.

Scheme 2

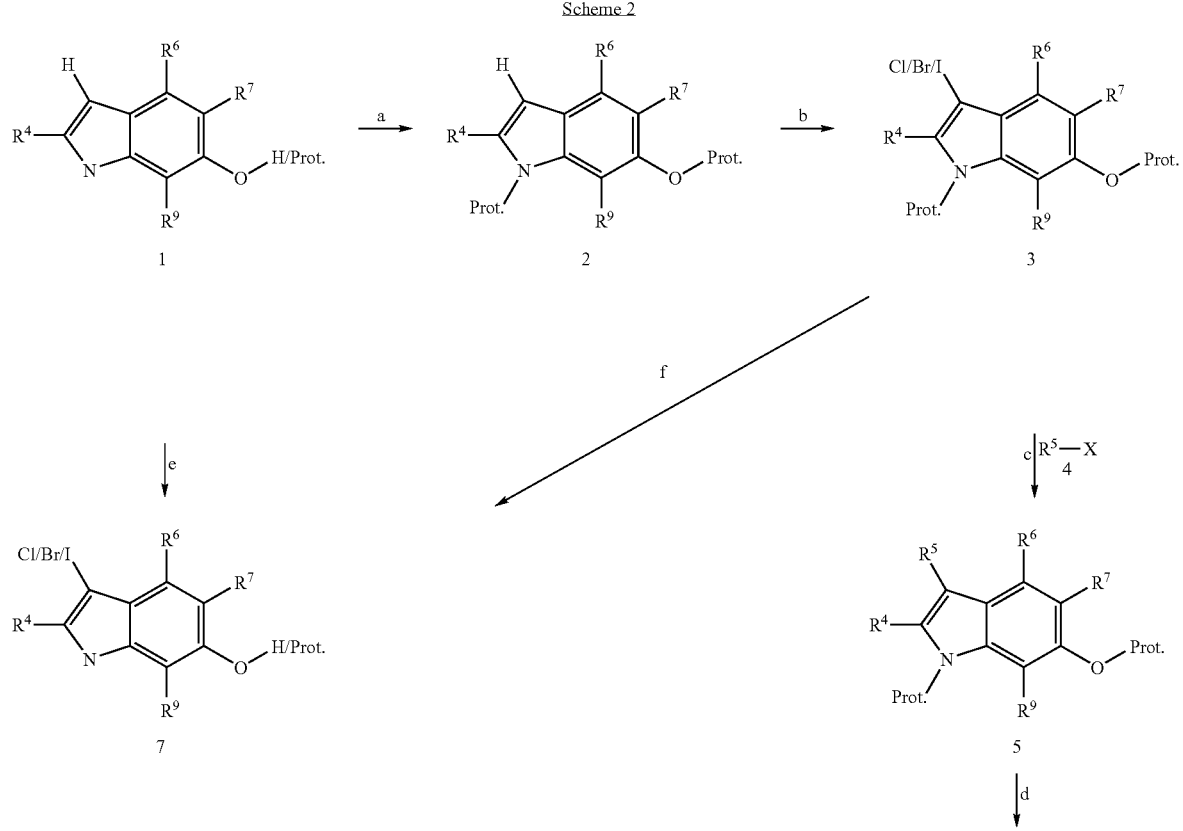

-continued

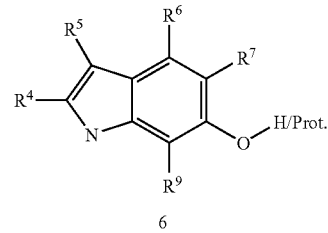

6

Introduction of a protecting group at the nitrogen atom of indols 1 can be performed under standard conditions, e.g. by deprotonation with a base like n-butyllithium, preferably at −78° C., and subsequent addition of e.g. tert-butyldimethylsilyl chloride at temperatures between −78° C. and ambient temperature in solvents like tetrahydrofuran (step a). Halogenation of protected indols 2, e.g. through reaction with N-bromosuccinimide at temperatures between −78° C. and ambient temperature in solvents like tetrahydrofuran delivers 3-halo indols 3 (step b). Compounds 3 can—following halogen metal exchange, preferably with tert-butyllithium at −78° C. in solvents like tetrahydrofuran—be reacted with alkylating reagents 4 with X e.g. being a chlorine, bromine or iodine atom, preferably with alkyl iodides, at temperatures between −78° C. and ambient temperature in solvents like tetrahydrofuran, to form indols 5 bearing a substituent in position 3 (step c). N-Deprotection or simultaneous N- and O-deprotection of compounds 5 leading to building blocks 6 can be performed by methods described in the literature, e.g. by treatment with tetrabutyl ammonium fluoride at temperatures between −15° C. and ambient temperature in a solvent like tetrahydrofuran, if the protecting groups are silyl ethers and/or silylated indoles (step d).

Building blocks 7 carrying a chlorine, bromine or iodine substituent in position 3 can be synthesized by halogenation of indols 1, optionally carrying a protecting group at the hydroxy function, e.g. by reaction with N-chlorosuccinimide at temperatures between −15° C. and the reflux temperature of the solvent in solvents like dichloromethane or chloroform (step e). Alternatively, the same halo-indols 7 can be obtained via N-deprotection or N- and O-deprotection of indols 3 as described in step d (step f).

Aryl-thiazoles 6 (scheme 1) are known or can be synthesized by methods known in the art. Representative examples of possible syntheses of these key intermediates are given in schemes 3–6.

Scheme 3

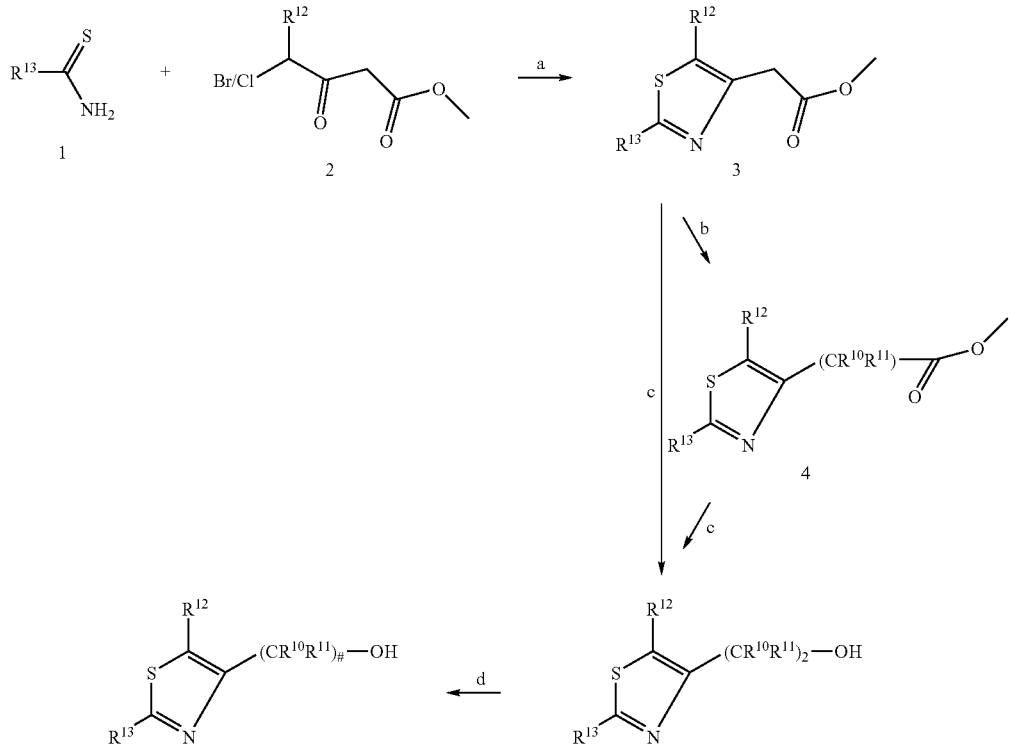

Thioamides 1 are known or can be prepared by methods known in the art, e.g. by treatment of the corresponding carboxamide with phosphorus pentasulfide or with Lawesson's reagent [2,4-bis(4-methoxyphenyl)-1,3-dithia-2,4-diphosphetane-2,4-disulfide] in a solvent like toluene at temperatures preferably between 60° C. and the reflux temperature of the solvent. Condensation of thioamides 1 with a suitable bis-electrophile, e.g. methyl 4-bromo- or 4-chloro-3-oxo-alkanoates 2, preferably in a solvent like toluene at elevated temperatures (e.g. at reflux temperature), gives thiazoles 3 carrying an acetic acid ester function at position 4 (step a) [compare PCT Int. Appl. (1997), WO97/31907 A1]. 4-Bromo-3-oxo-alkanoates 2 are known or can be prepared by methods known in the art [compare PCT Int. Appl. (2001), WO 01/79202 A1]. Thiazoles 3 can then be reduced, e.g. with lithium aluminum hydride in solvents like ether or tetrahydrofuran, to alcohols 5 with $R^{10}=R^{11}=H$ (step c). Alternatively, alkyl groups $R^{10}$ and/or $R^{11}$ can be introduced into ester compounds 3 by treatment with a base like potassium tert-butoxide or sodium hydride in solvents like tetrahydrofuran or 1,2-dimethoxyethane, followed by addition of one or sequentially two different alkyl halides, a reaction preferably performed between 0° C. and 80° C. (step b). Mono and/or dialkyl ester compounds 4 can be reduced to compounds 5, e.g. with lithium aluminum hydride in ether or tetrahydrofuran (step c). Alternatively, ester compounds 4 can be transformed into compounds 5 by i) saponification to the corresponding acid; ii) treatment with $R^{10}Li$, optionally in the presence of a Cu(I) salt, in ether or tetrahydrofuran to yield the alkyl ketones —$COR^{10}$; iii) subsequent reaction with $R^{11}Li$ or lithium aluminum hydride in ether or tetrahydrofuran (step c). Optionally, an elongation of the side chain can then be performed by standard methods such as transformation of the alcohol function into a leaving group, e.g. a mesylate, ensuing treatment with cyanide, saponification and reduction, affording thiazoles 6 with an optionally substituted hydroxy-propyl function attached to position 4 (step d). Alternatively, cyano intermediates of this elongation process can be reacted with alkyl Grignard reagents $R^{10}MgX$ in solvents like ether or tetrahydrofuran between 0° C. and the reflux temperature of the solvent to form the corresponding $R^{10}CO$-alkyl ketones, which upon treatment with an alkyllithium reagent $R^{11}Li$ or lithium aluminum hydride in solvents like ether or tetrahydrofuran give alcohols 6 (step d). The alcohol compounds 5 or 6 which contain one or more chiral centers can optionally be separated into optically pure antipodes by methods well known in the art, e.g. chromatography on a chiral HPLC column, or by derivatization with an optically pure acid to form esters, which can be separated by conventional HPLC chromatography and then converted back to the original alcohol. Alcohol compounds 5 or 6 correspond to or can be converted into compounds of general formula 6 (scheme 1), e.g. by treatment with methanesulfonyl chloride in dichloromethane in the presence of a base like triethylamine, preferably in a temperature range between –20° C. and room temperature, or e.g. by reaction with carbon tetrachloride or carbon tetrabromide and triphenylphosphine in solvents like tetrahydrofuran, preferably in a temperature range between room temperature and the reflux temperature of the solvents. By appropriately combining the above outlined methods, substituents $R^{10}$ and $R^{11}$ in 5 and 6 can be varied independently.

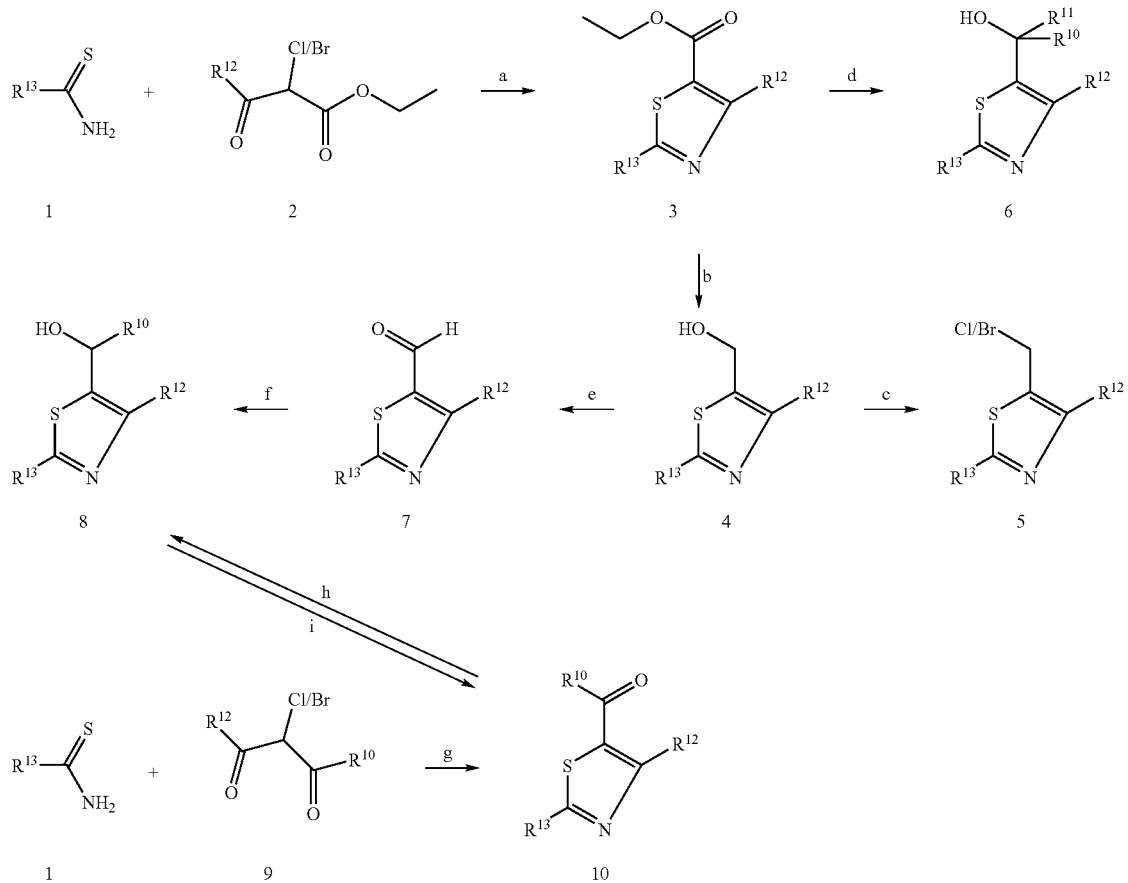

Scheme 4

Thioamides 1 can be reacted with 2-halo acetoacetates 2 in solvents like ethanol, preferably at reflux temperature, to give thiazole-carboxylic esters 3 (step a). 2-Halo acetoacetates 2 are known or can be prepared by methods known in the art [compare PCT Int. Appl. (2002), WO 02/062774 A1]. Reduction of these esters 3, preferably using lithium aluminum hydride in a solvent like ether or tetrahydrofuran, preferably between 0° C. and room temperature, gives primary alcohols 4 (step b), which can be used as such or can be converted into the corresponding halides 5, e.g. by treatment with methanesulfonyl chloride in dichloromethane in the presence of 2,6-lutidine, preferably between −20° C. and the reflux temperature of dichloromethane [ compare PCT Int. Appl. (2002), WO 02/28433], by treatment with thionyl chloride in a solvent like dichloromethane or chloroform, preferably at temperatures between −20° C. and +50° C., or by treatment with tetrabromomethane and triphenylphosphine in solvents like tetrahydrofuran at temperatures between 0° C. and the reflux temperature of tetrahydrofuran (step c). Esters 3 can be further converted into tertiary alcohols 6 with $R^{10}=R^{11}$ through reaction with alkyl organometallic reagents, preferably using alkyl Grignard compounds in a solvent like tetrahydrofuran or ether, preferably between −15° C. and the reflux temperature of the solvent [compare PCT Int. Appl. (2002), WO 02/062774 A1] (step d). Alcohols 6 with $R^{10}$ not equal to $R^{11}$ can be prepared by a sequential procedure: i) saponification to the acid; ii) treatment with $R^{10}$Li, optionally in the presence of a Cu(I) salt, in ether or tetrahydrofuran to yield the alkyl ketones —$COR^{10}$; iii) subsequent reaction with $R^{11}$Li or lithium aluminum hydride in ether or tetrahydrofuran (step d). Primary alcohols 4 can be oxidized to aldehydes 7 by methods known in the art, e.g. by treatment with pyridinium chlorochromate in dichloromethane, preferably at temperatures between room temperature and the reflux temperature of dichloromethane, or by treatment with manganese dioxide in solvents like dichloromethane, preferably at room temperature (step e). These aldehydes 7 can be converted to the corresponding secondary alcohols 8 through reaction with alkyl organometallic compounds, preferably under the conditions given for the transformation of esters 3 to tertiary alcohols 6 (step f).

Reaction of thioamides 1 with 2-halo 1,3-diketones 9 in solvents like ethanol, preferably at reflux temperature, gives thiazole ketones 10 (step g). Alternatively, ketones 10 can be obtained from secondary alcohols 8 by methods known in the art, e.g. by treatment with Cr(VI) reagents like the Jones reagent (Jones et al., *J. Chem. Soc.* 1953, 2548.) (step i). These ketones 10 can be reduced to the corresponding secondary alcohols 8 by methods known in the art, e.g. by treatment with sodium borohydride in alcohol, preferably at temperatures between −15° C. and 40° C. (step h). This reaction can also be carried out in an enantioselective fashion leading to the (R)- or (S)-alcohols 8, e.g. by treatment with borane-dimethylsulfide complex and (S)- or (R)-2-methyl-CBS-oxazaborolidine as chiral catalyst in tetrahydrofuran, preferably at temperatures between −78° C. and ambient temperature, according to Corey et al. (E. J. Corey, R. K. Bakshi, S. Shibata, *J. Am. Chem. Soc.* 1987, 109, 5551–5553), or by treatment with (+)- or (−)-B-chlorodiisopinocampheylborane (DIP-Cl), according to Brown et al. (P. V. Ramachandran, B. Gong, A. V. Teodorovic, H. C. Brown, *Tetrahedron: Asymmetry* 1994, 5, 1061–1074). If the alcohol compounds 4, 6, or 8 contain one or more chiral centers and are not optically pure, they can optionally be separated into optically pure antipodes by methods well known in the art, e.g. chromatography on a chiral HPLC column, or by derivatization with an optically pure acid to form esters, which can then be separated by conventional HPLC chromatography and converted back to the original alcohol.

The alcohol compounds 4, 6, and 8, and the halide compound 5, correspond to or can be converted into compounds of general formula 6 (scheme 1), e.g. by treatment with methanesulfonyl chloride in dichloromethane in the presence of a base like triethylamine preferably in a temperature range between −20° C. and room temperature, or e.g. by reaction with carbon tetrachloride or carbon tetrabromide and triphenylphosphine in solvents like tetrahydrofuran, preferably in a temperature range between room temperature and the reflux temperature of the solvents.

Scheme 5

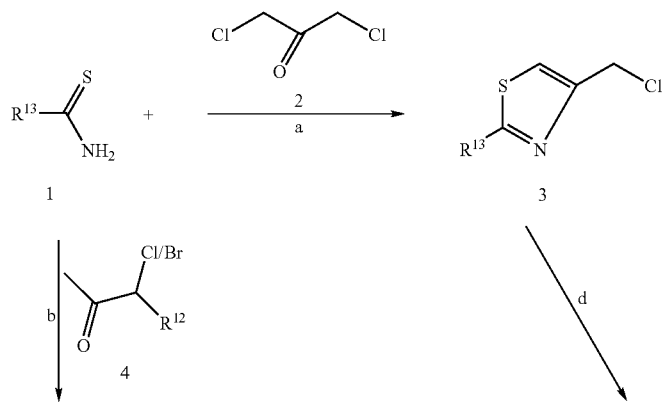

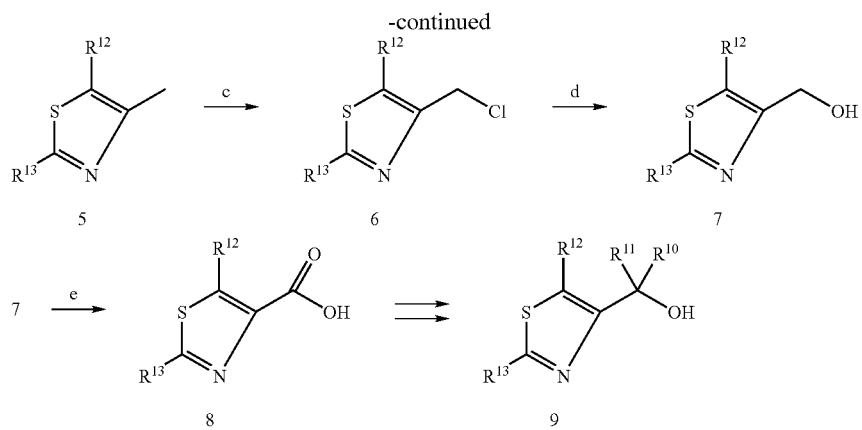

Thioamides 1 may be condensed with 1,3-dichloroacetone in solvents like acetone or acetonitrile between room temperature and the reflux temperature of the solvents, followed by treatment with a strong acid, e.g. concentrated sulfuric acid, preferably at ambient temperature (step a). Alternatively, thioamides 1 are condensed with alpha-bromo or alpha-chloro ketones 4 in a solvent like ethanol, preferably at reflux temperature, to give aryl-thiazoles 5 bearing a methyl function at position 4 (step b) [compare Eur. Pat. Appl. (1987), EP 207453 A2]. Derived chloromethyl compounds 6 are obtained by treatment of these aryl-thiazoles 5 with N-chlorosuccinimide in solvents like acetonitrile, preferably at reflux temperature, (step c) [compare PCT Int. Appl. (2001), WO 0119805 A1]. Chloromethyl compounds 3 and 6 can be converted into hydroxymethyl compounds 7, e.g. by formation of the primary acetates (e.g. with acetic acid in the presence of sodium iodide, potassium carbonate at elevated temperature) and subsequent saponification (e.g. with lithium hydroxide in ethanol/water at room temperature) (step d). Hydroxymethyl compounds 7 can be oxidized in one step to the corresponding acids 8, e.g. by use of oxidizing agents like chromic acid, alkali permanganate or nitric acid; alternatively, a two step procedure can be used: i) oxidation of the hydroxymethyl compounds 7 to the corresponding aldehydes using e.g. Swern conditions (oxalyl chloride/dimethylsulfoxide/triethylamine in dichloromethane, −78° C. to room temperature); ii) further oxidation to the acid compounds 8 by using e.g. sodium chlorite in an alcohol like tert-butanol and water in the presence of $NaH_2PO_4$ and 2-methyl-2-butene, preferably at room temperature (step e). Acid compounds 8 or the corresponding esters can be further transformed as described for ester 3 or the corresponding acids in scheme 4 to give the substituted alcohol compounds 9.

The alcohol compounds 7 and 9 and the halide compounds 3 and 6 correspond to or can be converted into compounds of general formula 6 (scheme 1), e.g. by treatment with methanesulfonyl chloride in dichloromethane in the presence of a base like triethylamine, preferably in a temperature range between −20° C. and room temperature, or e.g. by reaction with carbon tetrachloride or carbon tetrabromide and triphenylphosphine in solvents like tetrahydrofuran preferably in a temperature range between room temperature and the reflux temperature of the solvents. Chain elongation is feasible as detailed below in scheme 6.

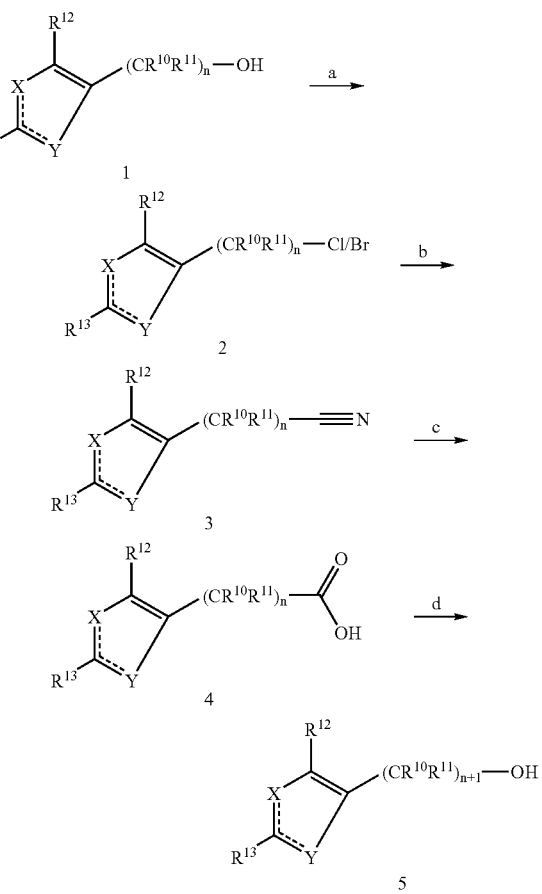

Aryl-thiazole alkanols 1 with a chain length of n carbon atoms can be converted into analogues with a chain length of n+1 carbon atoms by methods well known in the art, e.g. by conversion of the primary alcohol function into a suitable leaving group, e.g. a halide (step a), reaction with cyanide ion (step b), saponification (step c) followed by reduction of the acid formed (compounds 4) to the primary alcohols 5, e.g. by using diborane in tetrahydrofuran (step d). In order to introduce substituents $R^{10}$ and/or $R^{11}$ different from hydrogen, cyano intermediates 3 of this elongation process can be reacted with alkyl Grignard reagents $R^{10}MgX$ in solvents like ether or tetrahydrofuran between 0° C. and the reflux temperature of the solvent to form the corresponding $R^{10}CO$-alkyl ketones, which upon treatment with an alkyl-lithium reagent $R^{11}Li$ or lithium aluminum hydride in solvents like ether or tetrahydrofuran give alcohols 5. $R^{10}CO$-alkyl ketones can also be reduced, e.g. by treatment with sodium borohydride in alcohol, preferably at temperatures between −15° C. and 40° C. This reaction can also be carried out in an enantioselective fashion leading to the (R)- or (S)-alcohols 5, e.g. by treatment with borane-dimethylsulfide complex and (S)- or (R)-2-methyl-CBS-oxazaborolidine as chiral catalyst in tetrahydrofuran, preferably at temperatures between −78° C. and ambient temperature according to Corey et al. (E. J. Corey, R. K. Bakshi, S. Shibata, *J. Am. Chem. Soc.* 1987, 109, 5551–5553), or by treatment with (+)- or (−)-B-chlorodiisopinocampheylborane (DIP-Cl), according to Brown et al. (P. V. Ramachandran, B. Gong, A. V. Teodorovic, H. C. Brown, *Tetrahedron: Asymmetry* 1994, 5, 1061–1074). Alternatively, alcohol compounds 5 which contain one or more chiral centers can optionally be separated into optically pure antipodes by methods well known in the art, e.g. chromatography on a chiral HPLC column, or by derivatization with an optically pure acid to form esters, which can then be separated by conventional HPLC chromatography and converted back to the original alcohol. The alcohol compounds 5 correspond to or can be transformed into compounds of general formula 6 (scheme 1), e.g. by treatment with methanesulfonyl chloride in dichloromethane in the presence of a base like triethylamine, preferably in a temperature range between −20° C. and room temperature, or e.g. by reaction with carbon tetrachloride or carbon tetrabromide and triphenylphosphine in solvents like tetrahydrofuran, preferably in a temperature range between room temperature and the reflux temperature of the solvents.

The following tests were carried out in order to determine the activity of the compounds of formula (I).

Background information on the performed assays can be found in: Nichols J S et al. "Development of a scintillation proximity assay for peroxisome proliferator-activated receptor gamma ligand binding domain", (1998) Anal. Biochem. 257: 112–119.

Full-length cDNA clones for humans PPARδ and PPARα and mouse PPARγ were obtained by RT-PCR from human adipose and mouse liver cRNA, respectively, cloned into plasmid vectors and verified by DNA sequencing. Bacterial and mammalian expression vectors were constructed to produce glutathione-s-transferase (GST) and Gal4 DNA binding domain proteins fused to the ligand binding domains (LBD) of PPARδ (aa 139 to 442), PPARγ (aa 174 to 476) and PPARα (aa 167 to 469). To accomplish this, the portions of the cloned sequences encoding the LBDs were amplified from the full-length clones by PCR and then subcloned into the plasmid vectors. Final clones were verified by DNA sequence analysis.

Induction, expression, and purification of GST-LBD fusion proteins were performed in *E. coli* strain BL21 (pLysS) cells by standard methods (Ref: Current Protocols in Molecular Biology, Wiley Press, edited by Ausubel et al.).

Radioligand Binding Assay

PPARδ receptor binding was assayed in HNM10 (50 mM Hepes, pH 7.4, 10 mM NaCl, 5 mM $MgCl_2$, 0.15 mg/ml fatty acid-free BSA and 15 mM DTT). For each 96 well reaction a 500 ng equivalent of GST-PPARδ-LBD fusion protein and radioligand, e.g. 20000 dpm {2-methyl-4-[4-methyl-2-(4-trifluoromethyl-phenyl)-thiazol-5-yl-ditritiomethylsulfanyl]-phenoxy}-acetic acid, was bound to 10 µg SPA beads (PharmaciaAmersham) in a final volume of 50 µl by shaking. The resulting slurry was incubated for 1 h at RT and centrifuged for 2 min at 1300 g. The supernatant containing unbound protein was removed and the semidry pellet containing the receptor-coated beads was resuspended in 50 ul of HNM. Radioligand was added and the reaction incubated at RT for 1 h and scintillation proximity counting performed in the presence of test compounds was determined. All binding assays were performed in 96 well plates and the amount of bound ligand was measured on a Packard TopCount using OptiPlates (Packard). Dose response curves were done in triplicates within a range of concentration from $10^{-10}$ M to $10^{-4}$ M.

PPARα receptor binding was assayed in TKE50 (50 mM Tris-HCl, pH 8, 50 mM KCl, 2 mM EDTA, 0.1 mg/ml fatty acid-free BSA and 10 mM DTT). For each 96 well reaction an 140 ng equivalent of GST-PPARoa-LBD fusion protein was bound to 10 µg SPA beads (PharmaciaAmersham) in a final volume of 50 µl by shaking. The resulting slurry was incubated for 1 h at RT and centrifuged for 2 min at 1300 g. The supernatant containing unbound protein was removed and the semidry pellet containing the receptor-coated beads was resolved in 50 µl of TKE. For radioligand binding e.g. 10000 dpm of 2(S)-(2-benzoyl-phenylamino)-3-{4-[1,1-ditritio-2-(5-methyl-2-phenyl-oxazol-4-yl)-ethoxy]-phenyl}-propionic acid or 2,3-ditritio-2(S)-methoxy-3-{4-[2-(5-methyl-2-phenyl-oxazol-4-yl)-ethoxy]-benzo[b]thiophen-7-yl}-propionic acid in 50 ul were added, the reaction incubated at RT for 1 h and scintillation proximity counting performed. All binding assays were performed in 96 well plates and the amount of bound ligand measured on a Packard TopCount using OptiPlates (Packard). Nonspecific binding was determined in the presence of $10^{-4}$ M unlabelled compound. Dose response curves were done in triplicates within a range of concentration from $10^{-10}$ M to $10^{-4}$ M.

PPARγ receptor binding was assayed in TKE50 (50 mM Tris-HCl, pH 8, 50 mM KCl, 2 mM EDTA, 0.1 mg/ml fatty acid-free BSA and 10 mM DTT). For each 96 well reaction an 140 ng equivalent of GST-PPARγ-LBD fusion protein was bound to 10 µg SPA beads (PharmaciaAmersham) in a final volume of 50 ul by shaking. The resulting slurry was incubated for 1 h at RT and centrifuged for 2 min at 1300 g. The supernatant containing unbound protein was removed and the semidry pellet containing the receptor-coated beads was resolved in 50 ul of TKE. For radioligand binding e.g. 10000 dpm 2(S)-(2-benzoyl-phenylamino)-3-{4-[1,1-ditritio-2-(5-methyl-2-phenyl-oxazol-4-yl)-ethoxy]-phenyl}-propionic acid in 50 µl were added, the reaction incubated at RT for 1 h and scintillation proximity counting performed. All binding assays were performed in 96 well plates and the amount of bound ligand measured on a Packard TopCount using OptiPlates (Packard). Nonspecific binding was determined in the presence of $10^{-4}$ M unlabelled compound. Dose response curves were done in triplicates within a range of concentration from $10^{-10}$ M to $10^{-4}$ M.

Luciferase Transcriptional Reporter Gene Assays

Baby hamster kidney cells (BHK21 ATCC CCL10) were grown in DMEM medium containing 10% FBS at 37° C. in a 95%02:5% $CO_2$ atmosphere. Cells were seeded in 6 well plates at a density of $10^5$ Cells/well and then batch-transfected with either the pFA-PPARδ-LBD, pFA-PPARγ-LBD or pFA-PPARα-LBD expression plasmids plus a reporter plasmid. Transfection was accomplished with the Fugene 6 reagent (Roche Molecular Biochemicals) according to the suggested protocol. Six hours following transfection, the cells were harvested by trypsinization and seeded in 96 well plates at a density of $10^4$ cells/well. After 24 hours to allow attachment of cells, the medium was removed and replaced with 100 ul of phenol red-free medium containing the test substances or control ligands (final DMSO concentration: 0.1%). Following incubation of the cells for 24 hours with substances, 50 µl of the supernatant was discarded and then 50 µl of Luciferase Constant-Light Reagent (Roche Molecular Biochemicals) to lyse the cells and initiate the luciferase reaction was added. Luminescence for luciferase was measured in a Packard TopCount. Transcriptional activation in the presence of a test substance was expressed as fold-activation over cells incubated in the absence of the substance. EC50 values were calculated using the XLfit program (ID Business Solutions Ltd. UK).

The free acids of the compounds of the present invention ($R^1$ is hydrogen) exhibit $IC_{50}$ values of 0.1 nM to 10 µM, preferably 1 nM to 100 nM for PPARδ and $IC_{50}$ values of 1 nM to 10 µM, preferably 10 nM to 5 µM for PPARα. Compounds, in which $R^1$ is not hydrogen are converted in vivo to compounds in which $R^1$ is hydrogen. The following table shows measured values for some selected compounds of the present invention.

|  | PPARα $IC_{50}$ (µmol/l) | PPARγ $IC_{50}$ (µmol/l) | PPARδ $IC_{50}$ (µmol/l) |
| --- | --- | --- | --- |
| Example 2 | 2.23 | 10 | 0.024 |
| Example 8 | 0.227 | 10 | 0.042 |

The compounds of formula (I) and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula (I) and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1–500 mg, preferably 0.5–100 mg, of a compound of formula (I).

The following examples serve to illustrate the present invention in more detail. They are, however, not intended to limit its scope in any manner.

EXAMPLES

Abbreviations:

AcOEt=ethyl acetate, n-BuLi=n-butyllithium, DMF=N,N-dimethylformamide, DMPU=1,3-dimethyl-3,4,5,6-tetrahydro-2(1H)-pyrimidinone, HPLC=high performance liquid chromatography, LDA=lithium diisopropylamide, MeOH=methanol, quant. =quantitative, RT=room temperature, THF=tetrahydrofuran.

Example 1 a] 4-[4-Methyl-2-(4-trifluoromethyl-phenyl)-thiazol-5-ylmethoxy]-1H-indole

A mixture of 4-hydroxyindole (100 mg, 0.75 mmol), 5-chloromethyl-4-methyl-2-(4-trifluoromethyl-phenyl)-thiazole (219 mg, 0.75 mmol; PCT Int. Appl. (2002), WO 0262774 A1), cesium carbonate (489 mg, 1.5 mmol) and a trace of potassium iodide were suspended in acetone (10 ml). The suspension was stirred at ambient temperature for 14 h, the solvent evaporated under reduced pressure and the residue dissolved in 1 N HCl/ice water 1/1 and ethyl acetate. The layers were separated and the aqueous layer was extracted two times with ethyl acetate. The combined organic layers were washed two times with brine and dried over sodium sulfate. The solvent was removed under reduced pressure and the residue purified by column chromatography (silica gel, heptane/AcOEt) to give 130 mg (0.33 mmol, 45%) of the title compound as light yellow solid.

MS: 389.2 (M+H)$^+$, 320.4, 269.3.

b] {4-[4-Methyl-2-(4-trifluoromethyl-phenyl)-thiazol-5-ylmethoxy]-indol-1-yl}-acetic acid tert-butyl ester To a solution of 4-[4-methyl-2-(4-trifluoromethyl-phenyl)-thiazol-5-ylmethoxy]-1H-indole (50 mg, 130 µmol)

and bromo-acetic acid tert-butyl ester (20 µl, 140 µmol) in DMF (4 ml) was added sodium hydride (55%, 8 mg, 176 µmol) under an argon atmosphere at 0° C. The mixture was naturally warmed to room temperature, stirred for 72 h, poured onto 1 N HCl/ice water 1/1 and extracted three times with dichloromethane. The combined organic layers were washed with water and dried over sodium sulfate. The solvent was removed under reduced pressure and the residue purified by column chromatography (silica gel, heptane/AcOEt) to give 50 mg (99 µmol, 77%) of the title compound as light yellow oil.

MS: 525.2 (M+Na)$^+$, 503.3 (M+H)$^+$, 447.2, 256.1.

c] {4-[4-Methyl-2-(4-trifluoromethyl-phenyl)-thiazol-5-ylmethoxy]-indol-1-yl}-acetic acid To a solution of {4-[4-methyl-2-(4-trifluoromethyl-phenyl)-thiazol-5-ylmethoxy]-indol-1-yl}-acetic acid tert-butyl ester (50 mg, 99 µmol) in dichloromethane (4 ml) was added trifluoroacetic acid (1 ml). The reaction mixture was stirred for 2 h at ambient temperature. The solvent was removed under reduced pressure and the residue purified by preparative HPLC to give 5 mg (11 µmol, 11%) of the title compound as light yellow solid.

MS: 444.9 (M−H)$^−$, 401.1.

Example 2 a] [rac]-6-{1-[4-Methyl-2-(4-trifluoromethyl-phenyl)-thiazol-5-yl]-ethoxy}-1H-inode To a ice cold solution of 6-hydroxyindole (100 mg, 0.75 mmol), [rac]-1-[4-methyl-2-(4-trifluoromethyl-phenyl)-thiazol-5-yl]-ethanol (216 mg, 0.75 mmol; PCT Int. Appl. (2002), WO 02/062774 A1) and tributylphosphine (280 µl, 1.13 mmol) in tetrahydrofuran (5 ml) was added N,N,N',N'-tetramethyl azodicarboxamide (194 mg, 1.13 mmol). The cooling bath was removed and stirring continued for 14 h. The mixture was filtered over celite and the solvent removed under reduced pressure to give a light brown oil which was purified by column chromatography (silica gel, heptane/AcOEt) to give 52 mg (0.13 mmol, 17%) of the title compound as yellow oil.

MS: 403.3 (M+H)$^+$, 351.3, 269.3.

b] [rac]-(6-{1-[4-Methyl-2-(4-trifluoromethyl-phenyl)-thiazol-5-yl]-ethoxy}-indol-1-yl)-acetic acid tert-butyl ester In analogy to the procedure described in example 1 b], [rac]-6-{1-[4-methyl-2-(4-trifluoromethyl-phenyl)-thiazol-5-yl]-ethoxy}-1H-indole was reacted with bromo-acetic acid tert-butyl ester in the presence of sodium hydride in DMF to yield [rac]-(6-{1-[4-methyl-2-(4-trifluoromethyl-phenyl)-thiazol-5-yl]-ethoxy}-indol-1-yl)-acetic acid tert-butyl ester as colorless gum.

MS: 517.4 (M+H)$^+$.

c] [rac]-(6-{1-[4-Methyl-2-(4-trifluoromethyl-phenyl)-thiazol-5-yl]-ethoxy}-indol-1yl)-acetic acid To a solution of [rac]-(6-{1-[4-methyl-2-(4-trifluoromethyl-phenyl)-thiazol-5-yl]-ethoxy}-indol-1-yl)-acetic acid tert-butyl ester (30 mg, 58 µmol) in THF/methanol 2/1 (4.5 ml) was added a 1 N aqueous NaOH solution (1.5 ml). The reaction mixture was stirred for 14 h at ambient temperature, neutralized with 1 N aqueous HCl solution under ice cooling and concentrated under reduced pressure. The residue was dissolved in 1 N HCl/ice water 1/1 and ethyl acetate, the layers were separated and the aqueous layer was extracted with ethyl acetate. The combined organic layers were washed with ice water/brine 1/1, dried over sodium sulfate and the solvent was evaporated in vacuo to give the title compound (24 mg, 52 µmol, 90%) as light yellow oil.

MS: 459.3 (M−H)$^−$.

Example 3 a] [4-(tert-Butyl-dimethyl-silanyloxy)-indol-1-yl]-acetic acid tert-butyl ester

A dispersion of sodium hydride in mineral oil (55%, 61 mg, 1.4 mmol) was added to a solution of 4-(tert-butyl-dimethyl-silanyloxy)-1H-indole [251 mg, 1 mmol; Eur. Pat. Appl. (1986), EP 206225 A2] and bromo-acetic acid tert-butyl ester (160 µl. 1, 1.1 mmol) in N,N-dimethylformamide (10 ml) at 0° C. under an argon atmosphere. The reaction mixture was naturally warmed to ambient temperature, stirred for 14 h and cooled to 0° C. Ice water (10 ml) and concentrated HCl (2 ml) were added and the mixture was extracted three times with dichloromethane. The combined extracts were washed with brine and water and dried over sodium sulfate. The solvent was removed under reduced pressure to give a yellow liquid which was purified by column chromatography (silica gel, heptane/AcOEt) to give 246 mg (0.68 mmol, 67%) of the title compound as light yellow oil.

MS: 379.5 (M+NH$_4$)$^+$, 362.3 (M+H)$^+$.

b] (4-Hydroxy-indol-1-yl)-acetic acid tert-butyl ester

To an ice cooled solution of 198 mg (0.55 mmol) [4-(tert-butyl-dimethyl-silanyloxy)-indol-1-yl]-acetic acid tert-butyl ester in 2 ml of THF was added a 1 M solution of tetrabutylammonium fluoride hydrate in tetrahydrofuran (0.55 ml, 0.55 mmol). The reaction mixture was stirred for 1 h at ambient temperature. Diethyl ether was added and the ether solution was washed with saturated aqueous NH$_4$Cl solution, water and brine. Evaporation of the solvent under reduced pressure gave 49 mg (0.2 mmol, 36%) of (4-hydroxy-indol-1-yl)-acetic acid tert-butyl ester as white crystals.

MS: 265.5 (M+NH$_4$)$^+$, 248.4 (M+H)$^+$.

c] [rac]-(4-{2-Methyl-1-[4-methyl-2-(4-trifluoromethyl-phenyl)-thiazol-5-yl]-propoxy}-indol-1-yl)-acetic acid tert-butyl ester To an ice cold solution of (4-hydroxy-indol-1-yl)-acetic acid tert-butyl ester (49 mg, 0.2 mmol), [rac]-2-methyl-1-[4-methyl-2-(4-trifluoromethyl-phenyl)-thiazol-5-yl]-propan-1-ol [62 mg, 0.2 mmol; PCT Int. Appl. (2002), WO 02/062774 A1] and tributylphosphine (70 µl, 0.3 mmol) in tetrahydrofuran (3 ml) was added N,N,N',N'-tetramethyl azodicarboxamide (51 mg, 0.3 mmol) under an argon atmosphere. The cooling bath was removed and stirring continued for 14 h. Filtration over celite and evaporation of the solvent under reduced pressure gave a yellow oil which was purified by column chromatography (silica gel, heptane/AcOEt) to give 13 mg (24 µmol, 12%) of the title compound as yellow oil.

MS: 545.4 (M+H)$^+$.

d] [rac]-(4-{2-Methyl-1-[4-methyl-2-(4-trifluoromethyl-phenyl)-thiazol-5-yl]-propoxy}-indol-1-yl)-acetic acid In analogy to the procedure described in example 2 c], [rac]-(4-{2-methyl-1-[4-methyl-2-(4-trifluoromethyl-phenyl)-thiazol-5-yl]-propoxy}-indol-1-yl)-acetic acid tert-butyl ester was treated with NaOH to obtain [rac]-(4-{2-methyl-1-[4-methyl-2-(4-trifluoromethyl-phenyl)-thiazol-5-yl]-propoxy}-indol-1-yl)-acetic acid as yellow oil.

MS: 487.1 (M−H)⁻.

Example 4 a] [rac]-2-{4-[4-Methyl-2-(4-trifluoromethyl-phenyl)-thiazol-5-ylmethoxy]-indol-1-yl}-propionic acid tert-butyl ester In analogy to the procedure described in example 1 b], 4-[4-methyl-2-(4-trifluoromethyl-phenyl)-thiazol-5-ylmethoxy]-1H-indole (example 1 a]) was reacted with 2-bromo-propionic acid tert-butyl ester in the presence of sodium hydride to obtain [rac]-2-{4-[4-methyl-2-(4-trifluoromethyl-phenyl)-thiazol-5-ylmethoxy]-indol-1-yl}-propionic acid tert-butyl ester as yellow oil.

MS: 517.4 (M+H)⁺.

b] [rac]-2-{4-[4-Methyl-2-(4-trifluoromethyl-phenyl)-thiazol-5-ylmethoxy]-indol-1-yl}-propionic acid In analogy to the procedure described in example 2 c], [rac]-2-{4-[4-methyl-2-(4-trifluoromethyl-phenyl)-thiazol-5-ylmethoxy]-indol-1-yl}-propionic acid tert-butyl ester was treated with NaOH to obtain [rac]-2-{4-[4-methyl-2-(4-trifluoromethyl-phenyl)-thiazol-5-ylmethoxy]-indol-1-yl}-propionic acid as light yellow gum.

MS: 459.2 (M−H)⁻.

Example 5 a] [4-Methyl-2-(4-trifluoromethyl-phenyl)-thiazol-5-yl]-acetonitrile

Tetrabutylammonium cyanide (18.5 g, 67 mmol) was added to a solution of 5-chloromethyl-4-methyl-2-(4-trifluoromethyl-phenyl)-thiazole [15.0 g, 51 mmol; PCT Int. Appl. (2002), WO 0292590 A1] in acetonitrile (340 ml). The solution was stirred at ambient temperature for 16 h, saturated aqueous sodium bicarbonate solution/ice water 1/1 and ethyl acetate were added and the layers were separated. The aqueous layer was extracted with ethyl acetate, the combined organic layers were washed with ice water/brine 1/1, dried over sodium sulfate and the solvent was evaporated in vacuo to give a brown oil which was purified by column chromatography (silica gel, n-heptane/$CH_2Cl_2$) to yield 8.58 g (30 mmol, 59%) of the title compound as light yellow solid.

MS: 282.1 (M)⁺.

b] [4-Methyl-2-(4-trifluoromethyl-phenyl)-thiazol-5-yl]-acetic acid

A mixture of [4-methyl-2-(4-trifluoromethyl-phenyl)-thiazol-5-yl]-acetonitrile (8.86 g, 31 mmol), sodium hydroxide (12.5 g, 314 mmol), water (160 ml) and ethanol (160 ml) was stirred vigorously at 100° C. for 2.5 h. The reaction mixture was poured onto crushed ice and aqueous HCl and extracted three times with dichloromethane. The combined extracts were washed with water and brine, and dried over anhydrous sodium sulfate. Evaporation of the solvent under reduced pressure gave 9.5 g (quant.) of the title compound as light yellow solid.

MS: 302.0 (M+H)⁺.

c] 2-[4-Methyl-2-(4-trifluoromethyl-phenyl)-thiazol-5-yl]-ethanol

A solution of [4-methyl-2-(4-trifluoromethyl-phenyl)-thiazol-5-yl]-acetic acid (6.01 g, 20 mmol) in tetrahydrofuran (180 ml) was treated at 0° C. with a 1 M solution of $BH_3$*THF in tetrahydrofuran (49.8 ml, 49.8 mmol). The cooling bath was removed and the reaction mixture stirred at ambient temperature for 16 h. Careful quenching with MeOH and ice water, twofold extraction with AcOEt, washing with ice water/brine 1/1, drying over magnesium sulfate, and evaporation of the solvent left a crude product which was refluxed for 30 min in MeOH to liberate quantitatively the free alcohol. The solvent was evaporated in vacuo and the residue was purified by column chromatography (silica gel, dichloromethane/MeOH) to yield 5.68 g (20 mmol, 99%) of the title compound as yellow solid.

MS: 287.1 (M)⁺.

d] (4-{2-[4-Methyl-2-(4-trifluoromethyl-phenyl)-thiazol-5-yl]-ethoxy}-indol-1-yl)-acetic acid tert-butyl ester In analogy to the procedure described in example 3 c], (4-hydroxy-indol-1-yl)-acetic acid tert-butyl ester (example 3 b]) was reacted with 2-[4-methyl-2-(4-trifluoromethyl-phenyl)-thiazol-5-yl]-ethanol in the presence of triphenylphosphine and di-tert-butyl azodicarboxylate to yield (4-{2-[4-methyl-2-(4-trifluoromethyl-phenyl)-thiazol-5-yl]-ethoxy}-indol-1-yl)-acetic acid tert-butyl ester as white crystals.

MS: 517.4 (M+H)⁺.

e] (4-{2-[4-Methyl-2-(4-trifluoromethyl-phenyl)-thiazol-5-yl]-ethoxy}-indol-1-yl)-acetic acid In analogy to the procedure described in example 2 c], (4-{2-[4-methyl-2-(4-trifluoromethyl-phenyl)-thiazol-5-yl]-ethoxy}-indol-1-yl)-acetic acid tert-butyl ester was treated with NaOH to obtain (4-{2-[4-methyl-2-(4-trifluoromethyl-phenyl)-thiazol-5-yl]-ethoxy}-indol-1-yl)-acetic acid as white solid.

MS: 459.2 (M−H)⁻.

Example 6 a] [6-(tert-Butyl-dimethyl-silanyloxy)-indol-1-yl]-acetic acid tert-butyl ester

In analogy to the procedure described in example 1 b], 6-(tert-butyl-dimethyl-silanyloxy)-1H-indole was reacted with bromo-acetic acid tert-butyl ester in the presence of sodium hydride to obtain [6-(tert-butyl-dimethyl-silanyloxy)-indol-1-yl]-acetic acid tert-butyl ester as colorless liquid.

MS: 362.4 (M+H)⁺.

b] (6-Hydroxy-indol-1-yl)-acetic acid tert-butyl ester

In analogy to the procedure described in example 3 b], [6-(tert-butyl-dimethyl-silanyloxy)-indol-1-yl]-acetic acid tert-butyl ester was treated with tetrabutylammonium fluoride hydrate to obtain (6-hydroxy-indol-1-yl)-acetic acid tert-butyl ester as yellow oil.
MS: 265.5 $(M+NH_4)^+$, 248.4 $(M+H)^+$.

c] {6-[2-(4-Trifluoromethyl-phenyl)-thiazol-5-yl-methoxy]-indol-1-yl}-acetic acid tert-butyl ester In analogy to the procedure described in example 3 c], (6-hydroxy-indol-1-yl)-acetic acid tert-butyl ester was reacted with [2-(4-trifluoromethyl-phenyl)-thiazol-5-yl]-methanol [PCT Int. Appl. (2002), WO 02/062774 A1] in the presence of tributylphosphine and N,N,N',N'-tetramethyl azodicarboxamide to yield {6-[2-(4-trifluoromethyl-phenyl)-thiazol-5-ylmethoxy]-indol-1-yl}-acetic acid tert-butyl ester as white solid.
MS: 506.5 $(M+NH_4)^+$, 489.3 $(M+H)^+$.

d] {6-[2-(4-Trifluoromethyl-phenyl)-thiazol-5-yl-methoxy]-indol-1-yl}-acetic acid In analogy to the procedure described in example 2 c], {6-[2-(4-trifluoromethyl-phenyl)-thiazol-5-ylmethoxy]-indol-1-yl}-acetic acid tert-butyl ester was treated with NaOH to obtain {6-[2-(4-trifluoromethyl-phenyl)-thiazol-5-yl-methoxy]-indol-1-yl}-acetic acid as orange solid.
MS: 431.2 $(M-H)^-$.

Example 7 a] (6-{2-[4-Methyl-2-(4-trifluoromethyl-phenyl)-thiazol-5-yl]-ethoxy}-indol-1-yl)-acetic acid tert-butyl ester In analogy to the procedure described in example 3 c], (6-hydroxy-indol-1-yl)-acetic acid tert-butyl ester (example 6 b]) was reacted with 2-[4-methyl-2-(4-trifluoromethyl-phenyl)-thiazol-5-yl]-ethanol (example 5 c]) in the presence of triphenylphosphine and di-tert-butyl azodicarboxylate to yield (6-{2-[4-methyl-2-(4-trifluoromethyl-phenyl)-thiazol-5-yl]-ethoxy}-indol-1-yl)-acetic acid tert-butyl ester as light yellow oil.
MS: 517.4 $(M+H)^+$.

b] (6-{2-[4-Methyl-2-(4-trifluoromethyl-phenyl)-thiazol-5-yl]-ethoxy}-indol-1-yl)-acetic acid In analogy to the procedure described in example 2 c], (6-{2-[4-methyl-2-(4-trifluoromethyl-phenyl)-thiazol-5-yl]-ethoxy}-indol-1-yl)-acetic acid tert-butyl ester was treated with NaOH to obtain (6-{2-[4-methyl-2-(4-trifluoromethyl-phenyl)-thiazol-5-yl]-ethoxy}-indol-1-yl)-acetic acid as off-white solid.
MS: 459.2 $(M-H)^-$.

Example 8 a] 5-Iodomethyl-4-methyl-2-(4-trifluoromethyl-phenyl)-thiazole

A suspension of 5-chloromethyl-4-methyl-2-(4-trifluoromethyl-phenyl)-thiazole [4 g, 13.7 mmol; PCT Int. Appl. (2002), WO 0262774 A1] and sodium iodide (10.3 g, 68.6 mmol) in acetone (70 ml) was stirred at reflux temperature for 2 h under an argon atmosphere. The yellow precipitate was filtered off, the filtrate evaporated to dryness under reduced pressure and dissolved in tert-butyl methyl ether and brine/ice water 1/1. The aqueous layer was extracted one more time with tert-butyl methyl ether, the combined extracts washed with ice water/aqueous sodium thiosulfate, ice water/brine 1/1 and dried over sodium sulfate. The solvent was removed under reduced pressure and the residue recrystallized from tert-butyl methyl ether/heptane to give 2.5 g (6.5 mmol, 48%) of the title compound as yellow crystals.
MS: 383.9 $(M+H)^+$.

b] 3-[4-Methyl-2-(4-trifluoromethyl-phenyl)-thiazol-5-yl]-propionic acid ethyl ester A solution of ethyl acetate (2.24 ml, 22.8 mmol) in tetrahydrofuran (6 ml) was added to a −78° C. cold solution of LDA (2 M solution in tetrahydrofuran/n-heptane; 9.8 ml, 19.6 mmol) in tetrahydrofuran (15 ml) within 30 min under an argon atmosphere. The solution was stirred for 30 min at −78° C. and DMPU (3.9 ml, 32.6 mmol) was added within 20 min. A solution of 5-iodomethyl-4-methyl-2-(4-trifluoromethyl-phenyl)-thiazole (2.5 g, 6.5 mmol) in tetrahydrofuran (15 ml) was added within 30 min and stirring was continued for additional 30 min. The mixture was naturally warmed to ambient temperature, stirred for one hour and poured onto aqueous ammonium chloride/ice water 1/1. Twofold extraction with ethyl acetate was followed by washing of the combined extracts with ice water/brine 1/1 (two times), drying over sodium sulfate and removal of the solvent under reduced pressure. The residue was purified by column chromatography (silica gel, heptane/AcOEt) and crystallized from heptane/dichloro-methane to yield 480 mg (1.4 mmol, 21%) of the title compound as light yellow solid.
MS: 344.3 $(M+H)^+$.

c] 3-[4-Methyl-2-(4-trifluoromethyl-phenyl)-thiazol-5-yl]-propan-1-ol

A solution of 3-[4-methyl-2-(4-trifluoromethyl-phenyl)-thiazol-5-yl]-propionic acid ethyl ester (470 mg, 1.4 mmol) in tetrahydrofuran (5 ml) was added to a suspension of lithium aluminum hydride (53 mg, 1.4 mmol) in tetrahydrofuran (5 ml) under an argon atmosphere at ambient temperature within 5 min. The mixture was stirred for 5 h, cooled to 0° C. and treated cautiously with water (5 ml) and 10% aqueous NaOH (1 ml). The reaction mixture was filtered over celite, ice water/ethyl acetate 1/1 was added and the layers were separated. The aqueous layer was extracted one more time with ethyl acetate, the combined organic layers were washed with ice water/brine 1/1 and dried over sodium sulfate. Removal of the solvent under reduced pressure gave a yellow oil which was purified by column chromatography (silica gel, heptane/AcOEt) to yield 285 mg (950 µmol, 69%) of the title compound as colorless oil.
MS: 302.4 $(M+H)^+$.

d] (4-{3-[4-Methyl-2-(4-trifluoromethyl-phenyl)-thiazol-5-yl]-propoxy}-indol-1-yl)-acetic acid tert-butyl ester In analogy to the procedure described in example 3 c], (4-hydroxy-indol-1-yl)-acetic acid tert-butyl ester (example 3 b]) was reacted with 3-[4-methyl-2-(4-trifluoromethylphenyl)-thiazol-5-yl]-propan-1-ol in the presence of tributylphosphine and N,N,N',N'-tetramethyl azodicarboxamide to yield (4-{3-[4-methyl-2-(4-trifluoromethyl-phenyl)-thiazol-5-yl]-propoxy}-indol-1-yl)-acetic acid tert-butyl ester as colorless gum.

MS: 553.3 (M+Na)+, 531.4 (M+H)+.

e] (4-{3-[4-Methyl-2-(4-trifluoromethyl-phenyl)-thiazol-5-yl]-propoxy}-indol-1-yl) -acetic acid In analogy to the procedure described in example 2 c], (4-{3-[4-methyl-2-(4-trifluoromethyl-phenyl)-thiazol-5-yl]-propoxy}-indol-1-yl)-acetic acid tert-butyl ester was treated with NaOH to obtain (4-{3-[4-methyl-2-(4-trifluoromethyl-phenyl)-thiazol-5-yl]-propoxy}-indol-1-yl)-acetic acid as white solid.

MS: 473.0 (M–H)−.

Example 9 a] [rac]-(6-{2-Methyl-1-[4-methyl-2-(4-trifluoromethyl-phenyl)-thiazol-5-yl]-propoxy}-indol-1-yl)-acetic acid tert-butyl ester In analogy to the procedure described in example 3 c], (6-hydroxy-indol-1-yl)-acetic acid tert-butyl ester (example 6 b]) was reacted with [rac]-2-methyl-1-[4-methyl-2-(4-trifluoromethyl-phenyl)-thiazol-5-yl]-propan-1-ol [PCT Int. Appl. (2002), WO 02/062774 A1] in the presence of tributylphosphine and N,N,N',N'-tetramethyl azodicarboxamide to yield [rac]-(6-{2-methyl-1-[4-methyl-2-(4-trifluoromethyl-phenyl)-thiazol-5-yl]-propoxy}-indol-1-yl)-acetic acid tert-butyl ester as light yellow gum.

MS: 545.4 (M+H)+.

b] [rac]-(6-{2-Methyl-1-[4-methyl-2-(4-trifluoromethyl-phenyl)-thiazol-5-yl]-propoxy}-indol-1-yl)-acetic acid In analogy to the procedure described in example 2 c], [rac]-(6-{2-methyl-1-[4-methyl-2-(4-trifluoromethyl-phenyl)-thiazol-5-yl]-propoxy}-indol-1-yl)-acetic acid tert-butyl ester was treated with NaOH to obtain [rac]-(6-{2-methyl-1-[4-methyl-2-(4-trifluoromethyl-phenyl)-thiazol-5-yl]-propoxy}-indol-1-yl)-acetic acid as yellow solid.

MS: 487.0 (M–H)−.

Example 10 a] (6-{3-[4-Methyl-2-(4-trifluoromethyl-phenyl)-thiazol-5-yl]-propoxy}-indol-1-yl)-acid tert-butyl ester In analogy to the procedure described in example 3 c], (6-hydroxy-indol-1-yl)-acetic acid tert-butyl ester (example 6 b]) was reacted with 3-[4-methyl-2-(4-trifluoromethyl-phenyl)-thiazol-5-yl]-propan-1-ol (example 8 c]) in the presence of tributylphosphine and N,N,N',N'-tetramethyl azodicarboxamide to yield (6-{3-[4-methyl-2-(4-trifluoromethyl-phenyl)-thiazol-5-yl]-propoxy}-indol-1-yl)-acetic acid tert-butyl ester as colorless gum.

MS: 531.4 (M+H)+.

b] (6-{3-[4-Methyl-2-(4-trifluoromethyl-phenyl)-thiazol-5-yl]-propoxy}-indol-1-yl)-acid In analogy to the procedure described in example 2 c], (6-{3-[4-methyl-2-(4-trifluoromethyl-phenyl)-thiazol-5-yl]-propoxy}-indol-1-yl)-acetic acid tert-butyl ester was treated with LiOH to obtain (6-{3-[4-methyl-2-(4-trifluoromethyl-phenyl)-thiazol-5-yl]-propoxy}-indol-1-yl)-acetic acid as white solid.

MS: 473.0 (M–H)−.

Example 11 a] (S)-(6-{1-[4-Methyl-2-(4-trifluoromethyl-phenyl)-thiazol-5-yl]-ethoxy}-indol-1-yl)-acid tert-butyl ester In analogy to the procedure described in example 3 c], (6-hydroxy-indol-1-yl)-acetic acid tert-butyl ester (example 6 b]) was reacted with (R)-1-[4-methyl-2-(4-trifluoromethyl-phenyl)-thiazol-5-yl]-ethanol [ee=79%; PCT Int. Appl. (2002), WO 02/062774 A1] in the presence of tributylphosphine and N,N,N',N'-tetramethyl azodicarboxamide to obtain (S)-(6-{1-[4-methyl-2-(4-trifluoromethyl-phenyl)-thiazol-5-yl]-ethoxy}-indol-1-yl)-acetic acid tert-butyl ester as colorless liquid. The configuration was tentatively assigned as S according to R. Cadilla et al., PCT Int. Appl. (2002), WO 02/062774 A1 and the generally accepted $S_N2$-type mechanism of the Mitsunobu reaction.

MS: 517.3 (M+H)+.

b] (S)-(6-{1-[4-Methyl-2-(4-trifluoromethyl-phenyl)-thiazol-5-yl]-ethoxy}-indol-1-yl)-acetic acid In analogy to the procedure described in example 2 c], (S)-(6-{1-[4-methyl-2-(4-trifluoromethyl-phenyl)-thiazol-5-yl]-ethoxy}-indol-1-yl)-acetic acid tert-butyl ester was treated with LiOH to obtain (S)-(6-{1-[4-methyl-2-(4-trifluoromethyl-phenyl)-thiazol-5-yl]-ethoxy}-indol-1-yl)-acetic acid as orange oil. According to chiral HPLC (Chiralpak-ADH), the enantiomeric excess amounts to 69%.

MS: 459.2 (M–H)−.

Example 12 a] (R)-(6-{1-[4-Methyl-2-(4-trifluoromethyl-phenyl)-thiazol-5-yl]-ethoxy}-indol-1-yl)-acetic acid tert-butyl ester In analogy to the procedure described in example 3 c], (6-hydroxy-indol-1-yl)-acetic acid tert-butyl ester (example 6 b]) was reacted with (S)-1-[4-methyl-2-(4-trifluoromethyl-phenyl)-thiazol-5-yl]-ethanol [ee=95%; PCT Int. Appl. (2002), WO 02/062774 A1] in the presence of tributylphosphine and N,N,N',N'-tetramethyl azodicarboxamide to obtain (R)-(6-{1-[4-methyl-2-(4-trifluoromethyl-phenyl)-thiazol-5-yl]-ethoxy}-indol-1-yl)-acetic acid tert-butyl ester as colorless oil. The configuration was tentatively assigned as R according to R. Cadilla et al., PCT Int. Appl. (2002), WO 02/062774 A1 and the generally accepted $SN^2$-type mechanism of the Mitsunobu reaction.

MS: 517.3 (M+H)+.

b] (R)-(6-{1-[4-Methyl-2-(4-trifluoromethyl-phenyl)-thiazol-5-yl]-ethoxy}-indol-1-yl)-acetic acid In analogy to the procedure described in example 2 c], (R)-(6-{1-[4-methyl-2-(4-trifluoromethyl-phenyl)-thiazol-5-yl]-ethoxy}-indol-1-yl)-acetic acid tert-butyl ester was treated with LiOH to obtain (R)-(6-{1-[4-methyl-2-(4-trifluoromethyl-phenyl)-thiazol-5-yl]-ethoxy}-indol-1-yl)-acetic acid as light brown solid. According to chiral HPLC (Chiralpak-ADH), the enantiomeric excess amounts to 89%.
MS: 459.1 (M−H)⁻.

Example 13 a] [6-(5-Methyl-2-phenyl-thiazol-4-ylmethoxy)-indol-1-yl]-acetic acid tert-butyl ester In analogy to the procedure described in example 1 a], (6-hydroxy-indol-1-yl)-acetic acid tert-butyl ester (example 6 b]) was reacted with 4-bromomethyl-5-methyl-2-phenyl-thiazole [PCT Int. Appl. (2001), WO 0119805 A1] in the presence of cesium carbonate and potassium iodide in acetone for 14 h at ambient temperature to give the title compound as yellow oil.
MS: 435.3 (M+H)⁺.

b] [6-(5-Methyl-2-phenyl-thiazol-4-ylmethoxy)-indol-1-yl]-acetic acid

In analogy to the procedure described in example 2 c], [6-(5-methyl-2-phenyl-thiazol-4-ylmethoxy)-indol-1-yl]-acetic acid tert-butyl ester was treated with LiOH to obtain [6-(5-methyl-2-phenyl-thiazol-4-ylmethoxy)-indol-1-yl]-acetic acid as light yellow foam.
MS: 377.0 (M−H)⁻.

Example 14 a] 5-(tert-Butyl-dimethyl-silanyloxy)-1H-indole

A solution of 5-hydroxy-indol (5 g, 38 mmol), tert-butyldimethylsilyl chloride (6.13 g, 39.4 mmol) and imidazole (5.37 g, 68.1 mmol) in DMF (50 ml) was stirred for 20 h at RT. Diethyl ether was added and the mixture was washed with 1N HCl and water. The organic layer was dried over sodium sulfate and concentrated under reduced pressure to give 9.4 g (38 mmol, quant.) of 5-(tert-butyl-dimethyl-silanyloxy)-1H-indole.
MS: 248.1 (M+H)⁺.

b] [5-(tert-Butyl-dimethyl-silanyloxy)-indol-1-yl]-acetic acid ethyl ester

A suspension of 5-(tert-butyl-dimethyl-silanyloxy)-1H-indole (9.2 g, 37.2 mmol), ethyl bromoacetate (4.79 ml, 40.9 mmol) and cesium carbonate (36.4 g, 111.5 mmol) in DMF (140 ml) was stirred for 3 h at RT. Diethyl ether was added and the mixture was washed with 1N HCl and water, and dried over sodium sulfate. The ether phase was concentrated under reduced pressure to give 12.93 g (quant.) of [5-(tert-butyl-dimethyl-silanyloxy)-indol-1-yl]-acetic acid ethyl ester which was used in the next step without further purification.
MS: 334.1 (M+H)⁺.

c] (5-Hydroxy-indol-1-yl)-acetic acid ethyl ester

To an ice cold solution of [5-(tert-butyl-dimethyl-silanyloxy)-indol-1-yl]-acetic acid ethyl ester (12.9 g, 38.7 mmol) in THF (130 ml) was added tetrabutylammonium fluoride hydrate (12.5 g, 38.7 mmol). The reaction mixture was stirred for 1 h at RT, diluted with diethyl ether and washed with 1N HCl and water. Evaporation of the solvent under reduced pressure gave 7.07 g (32.2 mmol, 83%) of (5-hydroxy-indol-1-yl)-acetic acid ethyl ester.
MS: 220.1 (M+H)⁺.

d] [rac]-5-(1-Chloro-ethyl)-4-methyl-2-(4-trifluoromethyl-phenyl)-thiazole

To a solution of [rac]-1-[4-methyl-2-(4-trifluoromethyl-phenyl)-thiazol-5-yl]-ethanol (200 mg, 0.7 mmol; PCT Int. Appl. (2002), WO 02/062774 A1) in dichloromethane (2 ml) was added thionyl chloride (0.1 ml, 1.4 mmol) at −10° C. The cooling bath was removed after 10 min and stirring was continued for 30 min. The solvent was removed under reduced pressure and the residue dried under vacuo to give 220 mg (0.7 mmol, quant.) of the title compound as yellow solid which was used in the next step without further purification.

e] [rac]-(5-{1-[4-Methyl-2-(4-trifluoromethyl-phenyl)-thiazol-5-yl]-ethoxy}-indol-1-yl)-acetic acid ethyl ester In analogy to the procedure described in example 1 a], (5-hydroxy-indol-1-yl)-acetic acid ethyl ester was reacted with [rac]-5-(1-chloro-ethyl)-4-methyl-2-(4-trifluoromethyl-phenyl)-thiazole in the presence of cesium carbonate and potassium iodide in N,N-dimethylformamide for 4 h at ambient temperature to give the title compound as yellow solid.
MS: 489.1 (M+H)⁺.

f] [rac]-(5-{1-[4-Methyl-2-(4-trifluoromethyl-phenyl)-thiazol-5-yl]-ethoxy}-indol-1-yl)-acetic acid In analogy to the procedure described in example 2 c], [rac]-(5-{1-[4-methyl-2-(4-trifluoromethyl-phenyl)-thiazol-5-yl]-ethoxy}-indol-1-yl)-acetic acid ethyl ester was treated with LiOH to obtain [rac]-(5-{1-[4-methyl-2-(4-trifluoromethyl-phenyl)-thiazol-5-yl]-ethoxy}-indol-1-yl)-acetic acid as yellow solid.
MS: 459.3 (M−H)⁻.

Example 15 a] (6-{2-[5-Methyl-2-(4-trifluoromethyl-phenyl)-thiazol-4-yl]-ethoxy}-indol-1-yl)-acetic acid tert-butyl ester In analogy to the procedure described in example 3 c], (6-hydroxy-indol-1-yl)-acetic acid tert-butyl ester (example 6 b]) was reacted with 2-[5-methyl-2-(4-trifluoromethyl-phenyl)-thiazol-4-yl]-ethanol [PCT Int. Appl. (2001), WO 01/00603 A1] in the presence of triphenylphosphine and di-tert-butyl azodicarboxylate to yield (6-{2-[5-methyl-2-(4-trifluoromethyl-phenyl)-thiazol-4-yl]-ethoxy}-indol-1-yl)-acetic acid tert-butyl ester as colorless oil.
MS: 517.4 (M+H)⁺.

b] (6-{2-[5-Methyl-2-(4-trifluoromethyl-phenyl)-thiazol-4-yl]-ethoxy}-indol-1-yl)-acetic acid In analogy to the procedure described in example 2 c], (6-{2-[5-methyl-2-(4-trifluoromethyl-phenyl)-thiazol-4-yl]-ethoxy}-indol-1-yl)-acetic acid tert-butyl ester was treated with LiOH to obtain (6-{2-[5-methyl-2-(4-trifluoromethyl-phenyl)-thiazol-4-yl]-ethoxy}-indol-1-yl)-acetic acid as off-white crystals.
MS: 459.4 (M–H)⁻.

Example 16 a] [2-(4-Trifluoromethyl-phenyl)-thiazol-4-yl]-acetic acid methyl ester

A solution of [2-(4-trifluoromethyl-phenyl)-thiazol-4-yl]-acetic acid (3 g, 10.4 mmol) and p-toluenesulfonic acid mono-hydrate (0.5 g, 2.6 mmol) in methanol (30 ml) and trimethyl orthoformate (2 ml) was heated under reflux for 5 hours. After neutralization with aqueous sodium bicarbonate solution and evaporation of the solvents under reduced pressure, the residue was redissolved in tert-butyl methyl ether and dried over anhydrous sodium sulfate. Evaporation of the solvent gave 2.65 g (8.8 mmol, 84%) of [2-(4-trifluoromethyl-phenyl)-thiazol-4-yl]-acetic acid methyl ester as light brown solid.
MS: 302.2 (M+H)⁺.

b] 2-[2-(4-Trifluoromethyl-phenyl)-thiazol-4-yl]-ethanol

In analogy to the procedure described for example 8 c], [2-(4-trifluoromethyl-phenyl)-thiazol-4-yl]-acetic acid methyl ester was reduced with lithium aluminum hydride to give [2-(4-trifluoromethyl-phenyl)-thiazol-4-yl]-ethanol as white solid.

c] (6-{2-[2-(4-Trifluoromethyl-phenyl)-thiazol-4-yl]-ethoxy}-indol-1-yl)-acetic acid tert-butyl ester In analogy to the procedure described in example 3 c], (6-hydroxy-indol-1-yl)-acetic acid tert-butyl ester (example 6 b]) was reacted with 2-[2-(4-trifluoromethyl-phenyl)-thiazol-4-yl]-ethanol in the presence of triphenylphosphine and di-tert-butyl azodicarboxylate to yield (6-{2-[2-(4-trifluoromethyl-phenyl)-thiazol-4-yl]-ethoxy]-indol-1-yl)-acetic acid tert-butyl ester as yellow oil.
MS: 503.3 (M+H)⁺.

d] (6-{2-[2-(4-Trifluoromethyl-phenyl)-thiazol-4-yl]-ethoxy}-indol-1-yl)-acetic acid In analogy to the procedure described in example 2 c], (6-{2-[2-(4-trifluoromethyl-phenyl)-thiazol-4-yl]-ethoxy}-indol-1-yl)-acetic acid tert-butyl ester was treated with LiOH to obtain (6-{2-[2-(4-trifluoromethyl-phenyl)-thiazol-4-yl]-ethoxy}-indol-1-yl)-acetic acid as brown solid.
MS: 445.0 (M–H)⁻.

Example 17 a] 6-(tert-Butyl-dimethyl-silanyloxy)-3-chloro-1H-indole

A solution of N-chlorosuccinimide (270 mg, 2 mmol) in dichloromethane (4 ml) is added within 30 min to a solution of 6-(tert-butyl-dimethyl-silanyloxy)-1H-indole (500 mg, 2 mmol) in dichloromethane (10 ml) at 0° C. under an argon atmosphere. The solution was naturally warmed to ambient temperature and stirred for 2 h. Ice water was added and the mixture was extracted two times with tert-butyl methyl ether. The combined extracts were dried over sodium sulfate and the solvent was removed under reduced pressure to give 560 mg (1.98 mmol, 98%) of the title compound as red solid which was used in the next step without further purification.
MS: 282.2 (M+H)⁺.

b] [6-(tert-Butyl-dimethyl-silanyloxy)-3-chloro-indol-1-yl]-acetic acid tert-butyl ester In analogy to the procedure described in example 1 b], 6-(tert-butyl-dimethyl-silanyloxy)-3-chloro-1H-indole was reacted with bromo-acetic acid tert-butyl ester in the presence of cesium carbonate in DMF to obtain [6-(tert-butyl-dimethyl-silanyloxy)-3-chloro-indol-1-yl]-acetic acid tert-butyl ester as yellow oil.
MS: 504.4 (M+H)⁺.

c] (3-Chloro-6-hydroxy-indol-1-yl)-acetic acid tert-butyl ester

In analogy to the procedure described in example 3 b], [6-(tert-butyl-dimethyl-silanyloxy)-3-chloro-indol-1-yl]-acetic acid tert-butyl ester was treated with tetrabutylammonium fluoride hydrate to obtain (3-chloro-6-hydroxy-indol-1-yl)-acetic acid tert-butyl ester as colorless gum.
MS: 299.3 (M+NH₄)⁺, 282.2 (M+H)⁺.

d] (3-Chloro-6-{2-[4-methyl-2-(4-trifluoromethyl-phenyl)-thiazol-5-yl]-ethoxy}-indol-1-yl)-acetic acid tert-butyl ester In analogy to the procedure described in example 3 c], (3-chloro-6-hydroxy-indol-1-yl)-acetic acid tert-butyl ester was reacted with 2-[4-methyl-2-(4-trifluoromethyl-phenyl)-thiazol-5-yl]-ethanol (example 5 c]) in the presence of triphenylphosphine and di-tert-butyl azodicarboxylate to yield (3-chloro-6-{2-[4-methyl-2-(4-trifluoromethyl-phenyl)-thiazol-5-yl]-ethoxy}-indol-1-yl)-acetic acid tert-butyl ester as light yellow oil.
MS: 551.3 (M+H)⁺.

e] (3-Chloro-6-{2-[4-methyl-2-(4-trifluoromethyl-phenyl)-thiazol-5-yl]-ethoxy}-indol-1-yl)-acetic acid In analogy to the procedure described in example 2 c], (3-chloro-6-{2-[4-methyl-2-(4-trifluoromethyl-phenyl)-thiazol-5-yl]-ethoxy}-indol-1-yl)-acetic acid tert-butyl ester was treated with LiOH to obtain (3-chloro-6-{2-[4-methyl-2-(4-trifluoromethyl-phenyl)-thiazol-5-yl]-ethoxy}-indol-1-yl)-acetic acid as light yellow solid.
MS: 493.0 (M–H)⁻.

Example 18 a] [rac]-3-[1,3]Dioxan-2-yl-1-[4-methyl-2-(4-trifluoromethyl-phenyl)-thiazol-5yl]-propan-1-ol To a solution of 4-methyl-2-(4-trifluoromethyl-phenyl)-thiazole-5-carbaldehyde (200 mg, 0.74 mmol) in tetrahydrofuran (2 ml) was added slowly a 0.5 M solution of (1,3-dioxan-2-ylethyl)magnesiumbromide in tetrahydrofuran (2.06 ml, 1.03 mmol) at ambient temperature under an argon atmosphere. The reaction mixture was stirred 1 h at ambient temperature, saturated aqueous NH$_4$Cl solution was added (15 ml) and the mixture was extracted two times with ethyl acetate. The combined organic layers were washed two times with brine/ice water 1/1 and dried over sodium sulfate. The solvent was removed under reduced pressure to give 280 mg (0.72 mmol, 98%) of the title compound as colorless oil which was used in the next step without further purification.

MS: 388.2 (M+H)$^+$, 330.5.

b] [rac]-(6-{3-[1,3]Dioxan-2-yl-1-[4-methyl-2-(4-trifluoromethyl-phenyl) -thiazol-5-yl]-propoxy}-indol-1-yl)-acetic acid tert-butyl ester In analogy to the procedure described in example 3 c], (6-hydroxy-indol-1-yl)-acetic acid tert-butyl ester (example 6 b]) was reacted with [rac]-3-[1,3]dioxan-2-yl-1-[4-methyl-2-(4-trifluoromethyl-phenyl)-thiazol-5-yl]-propan-1-ol in the presence of tributylphosphine and N,N,N',N'-tetramethyl azodicarboxamide to obtain [rac]-(6-{3-dioxan-2-yl-1-[4-methyl-2-(4-trifluoromethyl-phenyl)-thiazol-5-yl]-propoxy}-indol-1-yl)-acetic acid tert-butyl ester as yellow oil.

MS: 617.6 (M+H)$^+$.

c] [rac]-(6-{3-[1,3]Dioxan-2-yl-1-[4-methyl-2-(4-trifluoromethyl-phenyl) -thiazol-5-yl]-propoxy}-indol-1-yl)-acetic acid In analogy to the procedure described in example 2 c], [rac]-(6-{3-[1,3]dioxan-2-yl-1-[4-methyl-2-(4-trifluoromethyl-phenyl)-thiazol-5-yl]-propoxy}-indol-1-yl)-acetic acid tert-butyl ester was treated with LiOH to obtain [rac]-(6-{3-[1,3]dioxan-2-yl-1-[4-methyl-2-(4-trifluoromethyl-phenyl)-thiazol-5-yl]-propoxy}-indol-1-yl)-acetic acid as yellow oil.

MS: 559.3 (M–H)$^-$.

Example 19 a] 4-Methyl-2-(3-trifluoromethyl-phenyl)-thiazole-5-carboxylic acid ethyl ester

A solution of 3-trifluoromethyl-thiobenzamide (5 g, 23.2 mmol) and ethyl 2-chloro-acetoacetate (3.2 ml, 23.2 mmol) in ethanol (300 ml) was heated at reflux temperature for 14 hours. The solvent was removed under reduced pressure and the residue partitioned between ice water and ethyl acetate. The layers were separated and the aqueous phase extracted two times with ethyl acetate. The combined extracts were washed two times with ice water/brine 1/1 and dried over sodium sulfate. The solvent was removed under reduced pressure to give a yellow oil which was purified by column chromatography (silica gel, cyclohexane/dichloromethane) to yield 5.1 g (16.2 mmol, 70%) of the title compound as colorless crystals.

MS: 316.1 (M+H)$^+$.

b] [4-Methyl-2-(3-trifluoromethyl-phenyl)-thiazol-5-yl]-methanol

In analogy to the procedure described in example 8 c], 4-methyl-2-(3-trifluoromethyl-phenyl)-thiazole-5-carboxylic acid ethyl ester was reduced with lithium aluminum hydride to give [4-methyl-2-(3-trifluoromethyl-phenyl)-thiazol-5-yl]-methanol as colorless liquid.

MS: 274.2 (M+H)$^+$.

c] 5-Chloromethyl-4-methyl-2-(3-trifluoromethyl-phenyl)-thiazole

To a solution of [4-methyl-2-(3-trifluoromethyl-phenyl)-thiazol-5-yl]-methanol (1.2 g, 4.4 mmol) in chloroform (7 ml) was added thionyl chloride (0.64 ml, 8.8 mmol) at –10° C. under an argon atmosphere. The reaction mixture was stirred for 30 min, saturated aqueous sodium bicarbonate solution/ice water 1/1 was added and the layers were separated. The aqueous layer was extracted two times with dichloromethane. The combined organic layers were washed with ice water/brine 1/1 and dried over sodium sulfate. The solvent was evaporated in vacuo to give the title compound (1.2 g, 4.1 mmol, 94%) as yellow oil which was used in the next step without further purification.

d] [4-Methyl-2-(3-trifluoromethyl-phenyl)-thiazol-5-yl]-acetonitrile

Tetrabutylammonium cyanide (1.44 g, 5.4 mmol) was added to a solution of 5-chloromethyl-4-methyl-2-(3-trifluoromethyl-phenyl)-thiazole (1.2 g, 4.1 mmol) in acetonitrile (27 ml). The solution was stirred at ambient temperature for 16 h, saturated aqueous sodium bicarbonate solution/ice water 1/1 and ethyl acetate were added and the layers were separated. The aqueous layer was extracted with ethyl acetate, the combined organic layers were washed with ice water/brine 1/1, dried over sodium sulfate and the solvent was evaporated in vacuo to give brown oil which was purified by column chromatography (silica gel, pentane/ethyl acetate) to yield 700 mg (2.5 mmol, 60%) of the title compound as orange oil.

e] [4-Methyl-2-(3-trifluoromethyl-phenyl)-thiazol-5-yl]-acetic acid

A suspension of [4-methyl-2-(3-trifluoromethyl-phenyl)-thiazol-5-yl]-acetonitrile (700 mg, 2.5 mmol) and sodium hydroxide (992 mg, 24.8 mmol) in water (4.5 ml) and ethanol (4.5 ml) was stirred vigorously at 85° C. for 14 h. The reaction mixture was then poured onto crushed ice and aqueous HCl and extracted three times with ethyl acetate. The combined extracts were washed with water and brine and dried over anhydrous sodium sulfate. Evaporation of the solvents under reduced pressure left 430 mg (1.4 mmol, 58%) [4-methyl-2-(3-trifluoromethyl-phenyl)-thiazol-5-yl]-acetic acid as yellow solid.

MS: 302.2 (M+H)$^+$.

f] 2-[4-Methyl-2-(3-trifluoromethyl-phenyl)-thiazol-5-yl]-ethanol

A solution of [4-methyl-2-(3-trifluoromethyl-phenyl)-thiazol-5-yl]-acetic acid (430 mg, 1.4 mmol) in tetrahydrofuran (6 ml) was treated at 0° C. with a 1 M solution of BH$_3$*THF in tetrahydrofuran (3.6 ml, 3.6 mmol). The cooling bath was removed and the reaction mixture stirred at ambient temperature for 16 h. Careful quenching with MeOH and ice water, twofold extraction with AcOEt, washing with ice water/brine 1/1, drying over magnesium sulfate, and evaporation of the solvent left a crude product which was refluxed for 30 min in MeOH to liberate quantitatively the free alcohol. The solvent was evaporated in vacuo and the residue was purified by column chromatography (silica gel, n-heptane/ethyl acetate) to yield 230 mg (0.8 mmol, 56%) of the title compound as yellow oil.

MS: 288.2 (M+H)$^+$.

g] (6-{2-[4-Methyl-2-(3-trifluoromethyl-phenyl)-thiazol-5-yl]-ethoxy}-indol-1-yl)-acetic acid tert-butyl ester In analogy to the procedure described in example 3 c], (6-hydroxy-indol-1-yl)-acetic acid tert-butyl ester (example 6 b]) was reacted with 2-[4-methyl-2-(3-trifluoromethyl-phenyl)-thiazol-5-yl]-ethanol in the presence of triphenylphosphine and di-tert-butyl azodicarboxylate to yield (6-{2-[4-methyl-2-(3-trifluoromethyl-phenyl)-thiazol-5-yl]-ethoxy}-indol-1-yl)-acetic acid tert-butyl ester as colorless oil.

MS: 571.5 (M+H)$^+$.

h] (6-{2-[4-Methyl-2-(3-trifluoromethyl-phenyl)-thiazol-5-yl]-ethoxy}-indol-1-yl)-acetic acid In analogy to the procedure described in example 2 c], (6-{2-[4-methyl-2-(3-trifluoromethyl-phenyl)-thiazol-5-yl]-ethoxy}-indol-1-yl)-acetic acid tert-butyl ester was treated with LiOH to obtain (6-{2-[4-methyl-2-(3-trifluoromethyl-phenyl)-thiazol-5-yl]-ethoxy}-indol-1-yl)-acetic acid as yellow solid.

MS: 459.1 (M−H)$^-$.

Example 20 a] {6-[2-(4-Methyl-2-phenyl-thiazol-5-yl)-ethoxy]-indol-1-yl}-acetic acid tert-butyl ester In analogy to the procedure described in example 3 c], (6-hydroxy-indol-1-yl)-acetic acid tert-butyl ester (example 6 b]) was reacted with 2-(4-methyl-2-phenyl-thiazol-5-yl)-ethanol [U. H. Lindberg, G. Bexell, B. Ulff, *Acta Pharmaceutica Suecica* 1971, 8, 49-58] in the presence of triphenylphosphine and di-tert-butyl azodicarboxylate to yield {6-[2-(4-methyl-2-phenyl-thiazol-5-yl)-ethoxy]-indol-1-yl}-acetic acid tert-butyl ester as colorless oil.

MS: 449.4 (M+H)$^+$.

b] {6-[2-(4-Methyl-2-phenyl-thiazol-5-yl)-ethoxy]-indol-1-yl}-acetic acid

In analogy to the procedure described in example 2 c], {6-[2-(4-methyl-2-phenyl-thiazol-5-yl)-ethoxy]-indol-1-yl}-acetic acid tert-butyl ester was treated with LiOH to obtain {6-[2-(4-methyl-2-phenyl-thiazol-5-yl)-ethoxy]-indol-1-yl}-acetic acid as off-white solid.

MS: 391.1 (M−H)_.

Example 21 a] 3-Bromo-1-(tert-butyl-dimethyl-silanyl)-6-(tert-butyl-dimethyl-silanyoxy)-1H-indole A 1.6 M solution of BuLi in pentane (6.57 ml, 10.5 mmol) was added to a solution of 6-(tert-butyl-dimethyl-silanyloxy)-1H-indole (2 g, 8.1 mmol) in THF (40 ml) at −78° C. within 20 min under an argon atmosphere. The reaction mixture was stirred for 20 min at −78° C. tert-Butyldimethylsilyl chloride (1.6 g, 10.5 mmol) was added and the reaction mixture was stirred for 10 min at −78° C. and for 1 h at RT. The mixture was chilled to −78° C., N-bromosuccinimide (1.6 g, 8.9 mmol) was added and stirring was continued for 1 h at −78° C. and for 1 h at RT. The solution was diluted with diethyl ether and washed with saturated aqueous NaHCO$_3$ solution and water. The ether phase was dried over sodium sulfate, concentrated under reduced pressure and the residue was purified by column chromatography (silica gel, n-heptane/ethyl acetate 1:19) to give 2.64 g (6 mmol, 74%) 3-bromo-1-(tert-butyl-dimethyl-silanyl)-6-(tert-butyl-dimethyl-silanyloxy)-1H-indole as brown solid.

MS: 440.4 (M+H)$^+$.

b] 1-(tert-Butyl-dimethyl-silanyl)-6-(tert-butyl-dimethyl-silanyloxy)-3-methyl-1H-indole A 1.5 M solution of tert-butyllithium in pentane (3.3 ml, 4.99 mmol) was added dropwise to a solution of 3-bromo-1-(tert-butyl-dimethyl-silanyl)-6-(tert-butyl-dimethyl-silanyloxy)-1H-indole (1 g, 2.27 mmol) in THF (6 ml) at −78° C. under an argon atmosphere. After 15 min methyl iodide (0.28 ml, 4.54 mmol) was added at −78° C. The reaction mixture was stirred for another 30 min at −78° C. and then for 2 h at RT. After quenching with saturated aqueous NaHCO$_3$ solution the reaction mixture was partitioned between ether and water. The ether phase was dried over sodium sulfate and concentrated in vacuo to give 863 mg (2.3 mmol, quant.) 1-(tert-butyl-dimethyl-silanyl)-6-(tert-butyl-dimethyl-silanyloxy)-3-methyl-1H-indole as red crystals.

c] 3-Methyl-1H-indol-6-ol

In analogy to the procedure described in example 3 b], 1-(tert-butyl-dimethyl-silanyl)-6-(tert-butyl-dimethyl-silanyloxy)-3-methyl-1H-indole was treated with tetrabutylammonium fluoride hydrate to obtain 3-methyl-1H-indol-6-ol as brown crystals.

MS: 146.0 (M−H)$^-$.

d] 3-Methyl-6-{2-[4-methyl-2-(4-trifluoromethyl-phenyl)-thiazol-5-yl]-ethoxy}-1H-indole In analogy to the procedure described in example 3 c], 3-methyl-1H-indol-6-ol was reacted with 2-[4-methyl-2-(4-trifluoromethyl-phenyl)-thiazol-5-yl]-ethanol (example 5 c]) in the presence of triphenylphosphine and di-tert-butyl azodicarboxylate to yield 3-methyl-6-{2-[4-methyl-2-(4-trifluoromethyl-phenyl)-thiazol-5-yl]-ethoxy}-1H-indole as yellow solid.

MS: 417.3 (M+H)$^+$.

e] (3-Methyl-6-{2-[4-methyl-2-(4-trifluoromethyl-phenyl)-thiazol-5-yl]-ethoxy}-indol-1-yl)-acetic acid tert-butyl ester In analogy to the procedure described in example 3 a], 3-methyl-6-{2-[4-methyl-2-(4-trifluoromethyl-phenyl)-thiazol-5-yl]-ethoxy}-1H-indole was reacted with tert-butyl bromoacetate in the presence of sodium hydride to obtain (3-methyl-6-{2-[4-methyl-2-(4-trifluoromethyl-phenyl)-thiazol-5-yl]-ethoxy}-indol-1-yl)-acetic acid tert-butyl ester as colorless gum.

MS: 531.6 (M+H)$^+$.

f] (3-Methyl-6-{2-[4-methyl-2-(4-trifluoromethyl-phenyl)-thiazol-5-yl]-ethoxy}-indol-1-yl)-acetic acid In analogy to the procedure described in example 2 c], (3-methyl-6-{2-[4-methyl-2-(4-trifluoromethyl-phenyl)-thiazol-5-yl]-ethoxy}-indol-1-yl)-acetic acid tert-butyl ester was treated with LiOH to obtain (3-methyl-6-{2-[4-methyl- 2-(4-trifluoromethyl-phenyl)-thiazol-5-yl]-ethoxy}-indol-1-yl)-acetic acid as off-white solid.

MS: 473.0 (M–H)_.

Example 22 a] 1-(tert-Butyl-dimethyl-silanyl)-6-(tert-butyl-dimethyl-silanyloxy)-3-propyl-1H-indole In analogy to the procedure described in example 21 b], 3-bromo-1-(tert-butyl-dimethyl-silanyl)-6-(tert-butyl-dimethyl-silanyloxy)-1H-indole (example 21 a]) was treated with tert-butyllithium and propyl iodide to yield 1-(tert-butyl-dimethyl-silanyl)-6-(tert-butyl-dimethyl-silanyloxy)-3-propyl-1H-indole as red liquid.

b] 3-Propyl-1H-indol-6-ol

In analogy to the procedure described in example 3 b], 1-(tert-butyl-dimethyl-silanyl)-6-(tert-butyl-dimethyl-silanyloxy)-3-propyl-1H-indole was treated with tetrabutylammonium fluoride hydrate to obtain 3-propyl-1H-indol-6-ol as white crystals.

MS: 176.3 (M+H)$^+$.

c] 6-{2-[4-Methyl-2-(4-trifluoromethyl-phenyl)-thiazol-5-yl]-ethoxy}-3-propyl-1H-indole In analogy to the procedure described in example 3 c], 3-propyl-1H-indol-6-ol was reacted with 2-[4-methyl-2-(4-trifluoromethyl-phenyl)-thiazol-5-yl]-ethanol (example 5 c]) in the presence of triphenylphosphine and di-tert-butyl azodicarboxylate to yield 6-{2-[4-methyl-2-(4-trifluoromethyl-phenyl)-thiazol-5-yl]-ethoxy}-3-propyl-1H-indole as yellow oil.

MS: 445.5 (M+H)$^+$.

d] (6-{2-[4-Methyl-2-(4-trifluoromethyl-phenyl)-thiazol-5-yl]-ethoxy}-3-propyl-indol-1-yl)-acetic tert-butyl ester In analogy to the procedure described in example 3 a], 6-{2-[4-methyl-2-(4-trifluoromethyl-phenyl)-thiazol-5-yl]-ethoxy}-3-propyl-1H-indole was reacted with tert-butyl bromoacetate in the presence of sodium hydride to obtain (6-{2-[4-methyl-2-(4-trifluoromethyl-phenyl)-thiazol-5-yl]-ethoxy}-3-propyl-indol-1-yl)-acetic acid tert-butyl ester as colorless oil.

MS: 559.3 (M+H)$^+$.

e] (6-{2-[4-Methyl-2-(4-trifluoromethyl-phenyl)-thiazol-5-yl]-ethoxy}-3-propyl-indol-1-yl)-acetic acid In analogy to the procedure described in example 2 c], (6-{2-[4-methyl-2-(4-trifluoromethyl-phenyl)-thiazol-5-yl]-ethoxy}-3-propyl-indol-1-yl)-acetic acid tert-butyl ester was treated with LiOH to obtain (6-{2-[4-methyl-2-(4-trifluoromethyl-phenyl)-thiazol-5-yl]-ethoxy]-3-propyl-indol-1-yl)-acetic acid as brown solid.

MS: 503.3 (M+H)$^+$.

Example 23 a] 4,5-Dimethyl-2-(4-trifluoromethyl-phenyl)-thiazole hydrochloride;

A solution of 4-trifluoromethyl-thiobenzamide (4 g, 19.5 mmol) and 3-chloro-2-butanone (3.9 ml, 39 mmol) in isopropanol (20 ml) was heated to reflux for 30 h under an argon atmosphere. The reaction mixture was concentrated to a volume of 10 ml, cooled to 50° C. and diisopropylether (20 ml) was added dropwise. The solution was cooled to ambient temperature, the resulting crystals were filtered off, washed with ice cold diisopropylether and dried in vacuo to give 2.6 g (8.9 mmol, 45%) of the title compound as off-white crystals.

MS: 258.4 (M+H)$^+$.

b] 4-Bromomethyl-5-methyl-2-(4-trifluoromethyl-phenyl)-thiazole 4,5-Dimethyl-2-(4-trifluoromethyl-phenyl)-thiazole hydrochloride (2.6 g, 8.9 mmol) was suspended in ethyl acetate and ice water. Triethylamine (1.2 ml, 8.9 mmol) was added, the organic layer was separated and the aqueous layer was extracted with ethyl acetate. The combined organic layers were washed with brine/ice water 1/1 dried over sodium sulfate and the solvent was removed under reduced pressure. The residue was dried in vacuo and dissolved in acetonitrile (30 ml) under an argon atmosphere. The solution was cooled to 0° C., N-bromosuccinimide (2.05 g, 11.5 mmol) and 2,2'-azobis(2-methylpropionitrile) (145 mg, 0.89 mmol) were added and the reaction mixture was stirred at ambient temperature for 14 h. Water was added and the formed precipitate was filtered off, washed with water and dried in vacuo to give yellow crystals. The crystals were purified by column chromatography (silica gel, n-heptane/dichloromethane) to give 385 mg (1.2 mmol, 13%) of the title compound as off-white crystals.

MS: 336.2 (M+H)$^+$.

c] {6-[5-Methyl-2-(4-trifluoromethyl-phenyl)-thiazol-4-ylmethoxyl]-indol-1-yl}-acetic acid tert-butyl ester In analogy to the procedure described in example 1 a], (6-hydroxy-indol-1-yl)-acetic acid tert-butyl ester (example 6 b]) was reacted with 4-bromomethyl-5-methyl-2-(4-trifluoromethyl-phenyl)-thiazole in the presence of cesium carbonate and potassium iodide in acetone for 72 h at ambient temperature to give the title compound as colorless oil.

MS: 503.3 (M+H)$^+$.

d] {6-[5-Methyl-2-(4-trifluoromethyl-phenyl)-thiazol-4-ylmethoxy]-indol-1-yl}-acetic acid In analogy to the procedure described in example 2 c], {6-[5-methyl-2-(4-trifluoromethyl-phenyl)-thiazol-4-ylmethoxy]-indol-1-yl}-acetic acid tert-butyl ester was treated with LiOH to obtain {6-[5-methyl-2-(4-trifluoromethyl-phenyl)-thiazol-4-ylmethoxy]-indol-1-yl}-acetic acid as yellow solid.

MS: 447.1 (M+H)$^+$.

Example 24 a] (6-{2-[4-Methyl-2-(4-trifluoromethoxy-phenyl)-thiazol-5-yl]-ethoxy}-indol-1-yl)-acid tert-butyl ester In analogy to the procedure described in example 3 c], (6-hydroxy-indol-1-yl)-acetic acid tert-butyl ester (example 6 b]) was reacted with 2-[5-methyl-2-(4-trifluoromethoxy-phenyl)-thiazol-4-yl]-ethanol {prepared from 4-methyl-2-(4-trifluoromethoxy-phenyl)-thiazole-5-carboxylic acid ethyl ester (PCT Int. Appl. (2001), WO 2001040207 A1) in analogy to the procedures described in examples 19 b] to 19 f]} in the presence of triphenylphosphine and di-tert-butyl azodicarboxylate to yield (6-{2-[4-methyl-2-(4-trifluoromethoxy-phenyl)-thiazol-5-yl]-ethoxy}-indol-1-yl)-acetic acid tert-butyl ester as yellow oil.

MS: 533.5 (M+H)$^+$.

b] (6-{2-[4-Methyl-2-(4-trifluoromethoxy-phenyl)-thiazol-5-yl]-ethoxy}-indol-1-yl)-acetic acid In analogy to the procedure described in example 2 c], (6-{2-[4-methyl-2-(4-trifluoromethoxy-phenyl)-thiazol-5-yl]-ethoxy}-indol-1-yl)-acetic acid tert-butyl ester was treated with LiOH to obtain (6-{2-[4-methyl-2-(4-trifluoromethoxy-phenyl)-thiazol-5-yl]-ethoxy}-indol-1-yl)-acetic acid as orange solid.

MS: 475.0 (M–H)$^-$.

Example 25 a] [rac]-1-[4-Methyl-2-(4-trifluoromethyl-phenyl)-thiazol-5-yl]-butane-1,4-diol To a solution of [rac]-1-[4-methyl-2-(4-trifluoromethyl-phenyl)-thiazol-5-yl]-but-3-en-1-ol [200 mg, 0.64 mmol; PCT Int. Appl. (2002), WO 02/062774 A1] in tetrahydrofuran (2 ml) was added a 1 M solution of borane-tetrahydrofuran complex in tetrahydrofuran (1.28 ml, 1.28 mmol) at ambient temperature under an argon atmosphere. The yellow solution was stirred for 1 h, water (1 ml), 3 M aqueous NaOH solution (0.2 ml) and 35% aqueous H$_2$O$_2$ solution (0.2 ml) were added and stirring was continued for 1 h. Water and ethyl acetate were added, the layers were separated and the aqueous layer was extracted with ethyl acetate. The combined organic layers were washed two times with brine and dried over sodium sulfate. The solvent was removed under reduced pressure to give 212 mg (0.64 mmol, quant.) of the title compound which was used in the next step without further purification.

MS: 332.3 (M+H)$^+$.

b] [rac]-4-(tert-Butyl-dimethyl-silanyloxy)-1-[4-methyl-2-(4-trifluoromethyl-phenyl)-thiazol-5-yl]-butan-1-ol tert-Butyl-dimethylsilyl chloride (115 mg, 0.76 mmol) was added in one portion to a stirred solution of [rac]-1-[4-methyl-2-(4-trifluoromethyl-phenyl)-thiazol-5-yl]-butane-1,4-diol (212 mg, 0.64 mmol) in pyridine (2 ml) at 0° C. The solution was naturally warmed to ambient temperature and stirred for 14 h. Pyridine was removed under reduced pressure and the residue dissolved in ethyl acetate. The solution was washed with 1 M aqueous HCl solution and two times with water and dried over sodium sulfate. The solvent was removed under reduced pressure and the residue was purified by column chromatography (silica gel, n-heptane/ethyl acetate) to give 120 mg (0.27 mmol, 42%) of the title compound as colorless crystals.

MS: 446.0 (M+H)$^+$.

c] [rac]-(6-{4-(tert-Butyl-dimethyl-silanyloxy)-1-[4-methyl-2-(4-trifluoromethyl-phenyl)-thiazol-5-yl]-butoxy}-indol-1-yl)-acetic acid tert-butyl ester In analogy to the procedure described in example 3 c], (6-hydroxy-indol-1-yl)-acetic acid tert-butyl ester (example 6 b]) was reacted with [rac]-4-(tert-butyl-dimethyl-silanyloxy)-1-[4-methyl-2-(4-trifluoromethyl-phenyl)-thiazol-5-yl]-butan-1-ol in the presence of tributylphosphine and N,N,N',N'-tetramethyl azodicarboxamide to obtain [rac]-(6-[4-(tert-butyl-dimethyl-silanyloxy)-1-[4-methyl-2-(4-trifluoromethyl-phenyl)-thiazol-5-yl]-butoxy}-indol-1-yl)-acetic acid tert-butyl ester as yellow oil.

MS: 675.3 (M+H)$^+$.

d] [rac]-(6-{4-Hydroxy-1-[4-methyl-2-(4-trifluoromethyl-phenyl)-thiazol-5-yl]-butoxy}-indol-1-yl)-acetic acid tert-butyl ester A 1 M solution of tetrabutylammonium fluoride hydrate (30 μl, 30 μmol) was added to an ice-cooled solution of [rac]-(6-[4-(tert-butyl-dimethyl-silanyloxy)-1-[4-methyl-2-(4-trifluoromethyl-phenyl)-thiazol-5-yl]-butoxy}-indol-1-yl)-acetic acid tert-butyl ester (17 mg, 25 μmol) in tetrahydrofuran (0.5 ml). The ice bath was removed and the solution stirred for 30 min at ambient temperature. Ethyl acetate was added and the solution was washed with 1 N HCl. The aqueous layer was extracted with ethyl acetate and the combined extracts were washed two times with brine and dried over sodium sulfate. Evaporation of the solvent gave 14 mg (25 μmol, quant.) of the title compound as yellow oil.

MS: 561.5 (M+H)$^+$.

e] [rac]-(6-{4-Hydroxy-1-[4-methyl-2-(4-trifluoromethyl-phenyl)-thiazol-5-yl]-butoxy}-indol-1-yl)-acetic acid In analogy to the procedure described in example 2 c], [rac]-(6-{4-hydroxy-1-[4-methyl-2-(4-trifluoromethyl-phenyl)-thiazol-5-yl]-butoxy}-indol-1-yl)-acetic acid tert-butyl ester was treated with LiOH to obtain [rac]-(6-{4-hydroxy-1-[4-methyl-2-(4-trifluoromethyl-phenyl)-thiazol-5-yl]-butoxy}-indol-1-yl)-acetic acid as brown crystals.

MS: 503.0 (M–H)$^-$.

Example 26 a] {6-[2-(5-Methyl-2-phenyl-thiazol-4-yl)-ethoxy]-indol-1-yl}-acetic acid tert-butyl ester In analogy to the procedure described in example 3 c], (6-hydroxy-indol-1-yl)-acetic acid tert-butyl ester (example 6 b]) was reacted with 2-(5-methyl-2-phenyl-thiazol-4-yl)-ethanol in the presence of triphenylphosphine and di-tert-butyl azodicarboxylate to yield {6-[2-(5-methyl-2-phenyl-thiazol-4-yl)-ethoxy]-indol-1-yl}-acetic acid tert-butyl ester as yellow oil.

MS: 449.0 (M+H)$^+$.

b] {6-[2-(5-Methyl-2-phenyl-thiazol-4-yl)-ethoxy]-indol-1-yl}-acetic acid

In analogy to the procedure described in example 2 c], {6-[2-(5-methyl-2-phenyl-thiazol-4-yl)-ethoxy]-indol-1-yl}-acetic acid tert-butyl ester was treated with LiOH to obtain {6-[2-(5-methyl-2-phenyl-thiazol-4-yl)-ethoxy]-indol-1-yl}-acetic acid as colorless solid.

MS: 391.0 (M–H)⁻.

Example 27 a] 5-(tert-Butyl-dimethyl-silanyloxy)-1H-indole

A suspension of 5-hydroxy-indol (5 g, 38 mmol), tert-butyldimethylsilyl chloride (6.1 g, 39.4 mmol) and imidazole (5.4 g, 68 mmol) in DMF (50 ml) was stirred for 20 h at RT. The reaction mixture was taken up in ether and washed with 1N HCl and water. The organic layer was dried over sodium sulfate and concentrated under reduced pressure to give 9.4 g (38 mmol, quant.) 5-(tert-butyl-dimethyl-silanyloxy)-1H-indole.

MS: 248.1 (M+H)⁺.

b] 3-Bromo-1-(tert-butyl-dimethyl-silanyl)-5-(tert-butyl-dimethyl-silanyloxy)-1H-indole A 1.6 M solution of BuLi in pentane (30.7 ml, 49.2 mmol) was added to a solution of 5-(tert-butyl-dimethyl-silanyloxy)-1H-indole (9.36 g, 37.8 mmol) in THF (190 ml) at −78° C. within 20 min under an argon atmosphere. The reaction mixture was stirred for 20 min at −78° C. tert-Butyldimethylsilyl chloride (7.64 g, 49.2 mmol) was added and the reaction mixture was stirred for 10 min at −78° C. and for 1 h at RT. The mixture was chilled to −78° C., N-bromosuccinimide (7.64 g, 41.6 mmol) was added and the solution was stirred for 1 h at −78° C. and for 1 h at RT. Diethyl ether was added and the mixture was washed with saturated aqueous NaHCO₃ solution and water. The organic layer was dried over sodium sulfate and concentrated under reduced pressure. The crude product was purified by column chromatography (silica gel, CH₂Cl₂/heptane 1:19) to give 12.87 g (29.2 mmol, 77%) 3-bromo-1-(tert-butyl-dimethyl-silanyl)-5-(tert-butyl-dimethyl-silanyloxy)-1H-indole.

MS: 442.2 (M+H)⁺.

c] 1-(tert-Butyl-dimethyl-silanyl)-5-(tert-butyl-dimethyl-silanyloxy)-3-ethyl-1H-indole A 1.5 M solution of tert-butyllithium in pentane (3.3 ml, 4.99 mmol) was added dropwise to a solution of 3-bromo-1-(tert-butyl-dimethyl-silanyl)-5-(tert-butyl-dimethyl-silanyloxy)-1H-indole (1 g, 2.3 mmol) in THF (6 ml) at −78° C. under an argon atmosphere. After 15 min ethyl iodide (0.37 ml, 4.5 mmol) was added at −78° C. The reaction mixture was stirred for 30 min at −78° C. and for 2 h at RT. After quenching with saturated aqueous NaHCO₃ solution the reaction mixture was partitioned between ether and water. The organic layer was dried over sodium sulfate and concentrated in vacuo to give 880 mg (2.26 mmol, 99%) 1-(tert-butyl-dimethyl-silanyl)-5-(tert-butyl-dimethyl-silanyloxy)-3-ethyl-1H-indole.

MS: 390.5 (M+H)⁺.

d] 3-Ethyl-1H-indol-5-ol

Tetrabutylammonium fluoride hydrate (1.4 g, 4.3 mmol) was added to an ice-cooled solution of 1-(tert-butyl-dimethyl-silanyl)-5-(tert-butyl-dimethyl-silanyloxy)-3-ethyl-1H-indole (840 mg, 2.2 mmol) in THF (8 ml). The reaction mixture was stirred for 45 min at ambient temperature, diluted with ethyl acetate and washed with 1 N HCl and water. The organic phase was concentrated under reduced pressure and the crude product purified by column chromatography (silica gel, ethyl acetate/heptane 1:2) to give 258 mg (1.6 mmol, 74%) 3-ethyl-1H-indol-5-ol.

e] 5-[4-Methyl-2-(4-trifluoromethyl-phenyl)-thiazol-5-ylmethoxy]-1H-indole

A suspension of 3-ethyl-1H-indol-5-ol (235 mg, 1.46 mmol), 5-chloromethyl-4-methyl-2-(4-trifluoromethyl-phenyl)-thiazole [425 mg, 1.46 mmol; PCT Int. Appl. (2002), WO 0292590 A1] and cesium carbonate (712 mg, 2.19 mmol) in DMF (3 ml) was stirred for 1.5 h at ambient temperature. Diethyl ether was added and the mixture was washed with 1N HCl and water. The organic layer was dried over sodium sulfate and concentrated under reduced pressure. The crude product was purified by column chromatography (silica gel, ethyl acetate/heptane 1:3) to give 522 mg (1.34 mmol, 86%) 5-[4-methyl-2-(4-trifluoromethyl-phenyl)-thiazol-5-ylmethoxy]-1H-indole.

MS: 417.3 (M+H)⁺.

f] {3-Ethyl-5-[4-methyl-2-(4-trifluoromethyl-phenyl)-thiazol-5-ylmethoxy]-indol-1-yl}-acetic acid ethyl ester A suspension of 5-[4-methyl-2-(4-trifluoromethyl-phenyl)-thiazol-5-ylmethoxy]-1H-indole (485 mg, 1.16 mmol), cesium carbonate (1.38 g, 3.49 mmol) and ethyl bromoacetate (0.15 ml, 1.28 mmol) in THF (5 ml) was stirred for 1.5 h at ambient temperature. Diethyl ether and 1N HCl/water 1/1 were added. The ether phase was dried over sodium sulfate and concentrated under reduced pressure to give 635 mg (1.26 mmol, 98%) {3-ethyl-5-[4-methyl-2-(4-trifluoromethyl-phenyl)-thiazol-5-ylmethoxy]-indol-1-yl}-acetic acid ethyl ester.

MS: 503.1 (M+H)⁺.

g] {3-Ethyl-5-[4-methyl-2-(4-trifluoromethyl-phenyl)-thiazol-5-ylmethoxy]-indol-1-yl}-acetic acid A 1 M aqueous solution of LiOH (2.3 ml, 2.3 mmol) was added to a solution of {3-ethyl-5-[4-methyl-2-(4-trifluoromethyl-phenyl)-thiazol-5-ylmethoxy]-indol-1-yl}-acetic acid ethyl ester (577 mg, 1.15 mmol) in THF (6 ml). After stirring for 1 h at ambient temperature, additional 0.58 ml of the 1N LiOH solution were added and the reaction mixture was stirred for further 2.5 h. Diethyl ether (10 ml) was added, the resulting precipitate was filtered off and redissolved in ethyl acetate and 25% aqueous HCl solution (2 ml). The organic layer was washed with water and dried over sodium sulfate. Removal of the solvent under reduced pressure gave 365 mg (0.77 mmol, 67%) {3-ethyl-5-[4-methyl-2-(4-trifluoromethyl-phenyl)-thiazol-5-ylmethoxy]-indol-1-yl}-acetic acid.

MS: 474.51 (M+H)⁺.

Example 28 a] 3-Butyl-1-(tert-butyl-dimethyl-silanyl)-5-(tert-butyl-dimethyl-silanyloxy)-1H-indole In analogy to the procedure described in example 27 c], 3-bromo-1-(tert-butyl-dimethyl-silanyl)-5-(tert-butyl-dimethyl-silanyloxy)-1H-indole was reacted with 1-iodobutane in the presence of tert-butyllithium to form 3-butyl-1-(tert-butyl-dimethyl-silanyl)-5-(tert-butyl-dimethyl-silanyloxy)-1H-indole as dark brown oil.

MS: 418 (M+H)$^+$.

b] {3-Butyl-5-[4-methyl-2-(4-trifluoromethyl-phenyl)-thiazol-5-ylmethoxy]-indol-1-yl}-acetic acid In analogy to the procedures described in example 27 d] to g], 3-butyl-1-(tert-butyl-dimethyl-silanyl)-5-(tert-butyl-dimethyl-silanyloxy)-1H-indole was transformed to {3-butyl-5-[4-methyl-2-(4-trifluoromethyl-phenyl)-thiazol-5-ylmethoxy]-indol-1-yl}-acetic acid.

MS: 503.0 (M+H)$^+$.

Example 29 a] 1-(tert-Butyl-dimethyl-silanyl)-5-(tert-butyl-dimethyl-silanyloxy)-3-methyl-1H-indole In analogy to the procedure described in example 27 c], 3-bromo-1-(tert-butyl-dimethyl-silanyl)-5-(tert-butyl-dimethyl-silanyloxy)-1H-indole was reacted with 1-iodomethane in the presence of tert-butyllithium to give 1-(tert-butyl-dimethyl-silanyl)-5-(tert-butyl-dimethyl-silanyloxy)-3-methyl-1H-indole as brown viscous oil.

MS: 376 (M+H)$^+$.

b] {3-Methyl-5-[4-methyl-2-(4-trifluoromethyl-phenyl)-thiazol-5-ylmethoxy]-indol-1-yl}-acetic acid In analogy to the procedures described in example 27 d] to g], 1-(tert-butyl-dimethyl-silanyl)-5-(tert-butyl-dimethyl-silanyloxy)-3-methyl-1H-indole was transformed to {3-methyl-5-[4-methyl-2-(4-trifluoromethyl-phenyl)-thiazol-5-ylmethoxy]-indol-1-yl}-acetic acid.

MS: 488.9 (M+H)$^+$.

Example 30 a] {6-[4-Methyl-2-(4-trifluoromethyl-phenyl)-thiazol-5-ylmethoxy]-indol-1-yl}-acetic acid tert-butyl ester In analogy to the procedure described in example 1 a], (6-hydroxy-indol-1-yl)-acetic acid tert-butyl ester (example 6 b]) was treated with 5-chloromethyl-4-methyl-2-(4-trifluoromethyl-phenyl)-thiazole [PCT Int. Appl. (2002), WO 0292590 A1] in the presence of cesium carbonate and potassium iodide in acetone for 14 h at reflux temperature to give the title compound as yellow liquid.

MS: 503.4 (M+H)$^+$.

b] {6-[4-Methyl-2-(4-trifluoromethyl-phenyl)-thiazol-5-ylmethoxy]-indol-1-yl}-acetic acid In analogy to the procedure described in example 2 c], {6-[4-methyl-2-(4-trifluoromethyl-phenyl)-thiazol-5-ylmethoxy]-indol-1-yl}-acetic acid tert-butyl ester was treated with LiOH to obtain {6-[4-methyl-2-(4-trifluoromethyl-phenyl)-thiazol-5-ylmethoxy]-indol-1-yl}-acetic acid as yellow solid.

MS: 445.0 (M−H)$^-$.

Example 31 a] 2,3-Difluoro-4-trifluoromethyl-thiobenzamide

A suspension of 2,3-difluoro-4-trifluoromethyl-benzamide (1 g, 4.4 mmol) and 2,4-bis(4-methoxyphenyl)-1,3-dithia-2,4-diphosphetane-2,4-disulfide (Lawesson's reagent; 900 mg, 2.2 mmol) in tetrahydrofuran (2 ml) was stirred under microwave irradiation at 130° C. for 15 min. The solvent was removed under reduced pressure to give an orange oil which was purified by column chromatography (silica gel, heptane/AcOEt) to yield 1.0 g (4.1 mmol, 93%) of the title compound as yellow crystals.

b] 2-(2,3-Difluoro-4-trifluoromethyl-phenyl)-4-methyl-thiazole-5-carboxylic acid ethyl ester A solution of 2,3-difluoro-4-trifluoromethyl-thiobenzamide (1.15 g, 4.8 mmol) and ethyl 2-chloro-acetoacetate (0.67 ml, 4.8 mmol) in ethanol (70 ml) was heated at reflux temperature for 14 hours. The solvent was removed under reduced pressure and the residue partitioned between ice water and ethyl acetate. The layers were separated and the aqueous phase extracted two more times with ethyl acetate. The combined extracts were washed two times with ice water/brine 1/1 and dried over sodium sulfate. The solvent was removed under reduced pressure to give a yellow oil which was purified by column chromatography (silica gel, heptane/AcOEt) to yield 700 mg (2 mmol, 42%) of the title compound as yellow crystals.

MS: 352.3 (M+H)$^+$.

c] [2-(2,3-Difluoro-4-trifluoromethyl-phenyl)-4-methyl-thiazol-5-yl]-methanol In analogy to the procedure described for example 8 c], 2-(2,3-difluoro-4-trifluoromethyl-phenyl)-4-methyl-thiazole-5-carboxylic acid ethyl ester was reduced with lithium aluminum hydride to give [2-(2,3-difluoro-4-trifluoromethyl-phenyl)-4-methyl-thiazol-5-yl]-methanol as white solid.

MS: 310.2 (M+H)$^+$.

d] 5-Chloromethyl-2-(2,3-difluoro-4-trifluoromethyl-phenyl)-4-methyl-thiazole To a solution of [2-(2,3-difluoro-4-trifluoromethyl-phenyl)-4-methyl-thiazol-5-yl]-methanol (45 mg, 150 µmol) in chloroform (3 ml) was added thionyl chloride (20 µl, 290 µmol) at −10° C. under an argon atmosphere. The reaction mixture was stirred for 30 min, saturated aqueous sodium bicarbonate solution/ice water 1/1 was added and the layers were separated. The aqueous layer was extracted two times with dichloromethane. The combined organic layers were washed with ice water/brine 1/1 and dried over sodium sulfate. The solvent was evaporated in vacuo to give the title compound (44 mg, 134 µmol, 90%) as yellow oil which was used in the next step without further purification.

e] {6-[2-(2,3-Difluoro-4-trifluoromethyl-phenyl)-4-methyl-thiazol-5-ylmethoxy]-indol-1-yl}-acetic acid tert-butyl ester In analogy to the procedure described in example 1 a], (6-hydroxy-indol-1-yl)-acetic acid tert-butyl ester (example 6 b]) was reacted with 5-chloromethyl-2-(2,3-difluoro-4-trifluoromethyl-phenyl)-4-methyl-thiazole in the presence of cesium carbonate and potassium iodide to obtain {6-[2-(2,3-difluoro-4-trifluoromethyl-phenyl)-4-methyl-thiazol-5-ylmethoxy]-indol-1-yl}-acetic acid tert-butyl ester as colorless liquid.

f] {6-[2-(2,3-Difluoro-4-trifluoromethyl-phenyl)-4-methyl-thiazol-5-ylmethoxy]-indol-1-yl}-acetic acid In analogy to the procedure described in example 2 c], {6-[2-(2,3-difluoro-4-trifluoromethyl-phenyl)-4-methyl-thiazol-5-ylmethoxy]-indol-1-yl}-acetic acid tert-butyl ester was treated with LiOH to obtain {6-[2-(2,3-difluoro-4-trifluoromethyl-phenyl)-4-methyl-thiazol-5-ylmethoxy]-indol-1-yl}-acetic acid as yellow solid.

MS: 481.2 (M–H)$^-$.

Example 32 a] {2-Methyl-5-[4-methyl-2-(4-trifluoromethyl-phenyl)-thiazol-5-ylmethoxy]-indol-1-yl}-acetic acid ethyl ester In analogy to the procedures described in example 27 e] and 27 f], 5-hydroxy-2-methylindole gave {2-methyl-5-[4-methyl-2-(4-trifluoromethyl-phenyl)-thiazol-5-ylmethoxy]-indol-1-yl}-acetic acid ethyl ester as light yellow powder.

MS: 489 (M+H)$^+$.

b] {2-Methyl-5-[4-methyl-2-(4-trifluoromethyl-phenyl)-thiazol-5-ylmethoxy]-indol-1-yl}-acetic acid In analogy to the procedure described in example 2 c], {2-methyl-5-[4-methyl-2-(4-trifluoromethyl-phenyl)-thiazol-5-ylmethoxy]-indol-1-yl}-acetic acid ethyl ester was treated with LiOH to obtain {2-methyl-5-[4-methyl-2-(4-trifluoromethyl-phenyl)-thiazol-5-ylmethoxy]-indol-1-yl}-acetic acid as off-white powder.

MS: 459 (M–H)$^-$; MP: 187–188° C., dec.

Example 33 a] {6-[2-(3-Fluoro-4-trifluoromethyl-phenyl)-4-methyl-thiazol-5-ylmethoxy]-indol-1-yl}-acetic acid tert-butyl ester In analogy to the procedure described in example 3 b], (6-hydroxy-indol-1-yl)-acetic acid tert-butyl ester (example 6 b]) was reacted with [2-(3-fluoro-4-trifluoromethyl-phenyl)-4-methyl-thiazol-5-yl]-methanol [PCT Int. Appl. (2002), WO 0228434 A2] in the presence of tributylphosphine and N,N,N',N'-tetramethyl azodicarboxamide to obtain {6-[2-(3-fluoro-4-trifluoromethyl-phenyl)-4-methyl-thiazol-5-ylmethoxy]-indol-1-yl}-acetic acid tert-butyl ester as light yellow gum.

MS: 521.3 (M+H)$^+$.

b] {6-[2-(3-Fluoro-4-trifluoromethyl-phenyl)-4-methyl-thiazol-5-ylmethoxy]-indol-1-yl}-acetic acid In analogy to the procedure described in example 2 c], {6-[2-(3-fluoro-4-trifluoromethyl-phenyl)-4-methyl-thiazol-5-ylmethoxy]-indol-1-yl}-acetic acid tert-butyl ester was treated with LiOH to obtain {6-[2-(3-fluoro-4-trifluoromethyl-phenyl)-4-methyl-thiazol-5-ylmethoxy]-indol-1-yl}-acetic acid as off-white solid.

MS: 463.0 (M–H)$^-$.

Example 34 a] 6-(tert-Butyl-dimethyl-silanyloxy)-3-chloro-1H-indole

A solution of N-chlorosuccinimide (270 mg, 2 mmol) in dichloromethane (4 ml) is added within 30 min to a solution of 6-(tert-butyl-dimethyl-silanyloxy)-1H-indole (500 mg, 2 mmol) in dichloromethane (10 ml) at 0° C. under an argon atmosphere. The solution was naturally warmed to ambient temperature and stirred for 2 h. Ice water was added and the mixture was extracted two times with tert-butyl methyl ether. The combined extracts were dried over sodium sulfate and the solvent was removed under reduced pressure to give 560 mg (1.98 mmol, 98%) of the title compound as red solid which was used in the next step without further purification.

MS: 282.2 (M+H)$^+$.

b] [6-(tert-Butyl-dimethyl-silanyloxy)-3-chloro-indol-1-yl]-acetic acid tert-butyl ester In analogy to the procedure described in example 1 b], 6-(tert-butyl-dimethyl-silanyloxy)-3-chloro-1H-indole was reacted with bromo-acetic acid tert-butyl ester in the presence of cesium carbonate in DMF to obtain [6-(tert-butyl-dimethyl-silanyloxy)-3-chloro-indol-1-yl]-acetic acid tert-butyl ester as yellow oil.

MS: 504.4 (M+H)$^+$.

c] (3-Chloro-6-hydroxy-indol-1-yl)-acetic acid tert-butyl ester

In analogy to the procedure described in example 3 b], [6-(tert-butyl-dimethyl-silanyloxy)-3-chloro-indol-1-yl]-acetic acid tert-butyl ester was treated with tetrabutylammonium fluoride hydrate to obtain (3-chloro-6-hydroxy-indol-1-yl)-acetic acid tert-butyl ester as colorless gum.

MS: 299.3 (M+NH$_4$)$^+$, 282.2 (M+H)$^+$.

d] {3-Chloro-6-[4-methyl-2-(4-trifluoromethyl-phenyl)-thiazol-5-ylmethoxy]-indol-1-yl}-acetic acid tert-butyl ester In analogy to the procedure described in example 1 a], (3-chloro-6-hydroxy-indol-1-yl)-acetic acid tert-butyl ester was reacted with 5-chloromethyl-4-methyl-2-(4-trifluoromethyl-phenyl)-thiazole [PCT Int. Appl. (2002), WO 0292590 A1] in the presence of cesium carbonate and potassium iodide in acetone for 14 h at ambient temperature to give the title compound as yellow crystals.

MS: 537.3 (M+H)$^+$.

e] {3-Chloro-6-[4-methyl-2-(4-trifluoromethyl-phenyl)-thiazol-5-ylmethoxy]-indol-1-yl}-acetic acid In analogy to the procedure described in example 2 c], {3-chloro-6-[4-methyl-2-(4-trifluoromethyl-phenyl)-thiazol-5-ylmethoxy]-indol-1-yl}-acetic acid tert-butyl ester was treated with LiOH to obtain {3-chloro-6-[4-methyl-2-(4-trifluoromethyl-phenyl)-thiazol-5-ylmethoxy]-indol-1-yl}-acetic acid as off-white solid.

MS: 479.0 (M–H)$^-$.

Example 35 a] 3-Bromo-1-(tert-butyl-dimethyl-silanyl)-6-(tert-butyl-dimethyl-silanyloxy)-1H-indole In analogy to the procedure described in example 27 b], 6-(tert-butyl-dimethyl-silanyloxy)-1H-indole was reacted with tert-butyldimethylsilyl chloride and subsequently with N-bromosuccinimide to obtain 3-bromo-1-(tert-butyl-dimethyl-silanyl)-6-(tert-butyl-dimethyl-silanyloxy)-1H-indole as brown solid.

MS: 440.4 (M+H)$^+$.

b] 1-(tert-Butyl-dimethyl-silanyl)-6-(tert-butyl-dimethyl-silanyloxy)-3-methyl-1H-indole In analogy to the procedure described in example 27 c], 3-bromo-1-(tert-butyl-dimethyl-silanyl)-6-(tert-butyl-dimethyl-silanyloxy)-1H-indole was treated with tert-butyl-lithium and methyl iodide to yield 1-(tert-butyl-dimethyl-silanyl)-6-(tert-butyl-dimethyl-silanyloxy)-3-methyl-1H-indole as red crystals.

c] 3-Methyl-1H-indol-6-ol

In analogy to the procedure described in example 27 d], 1-(tert-butyl-dimethyl-silanyl)-6-(tert-butyl-dimethyl-silanyloxy)-3-methyl-1H-indole was treated with tetrabutylammonium fluoride hydrate to obtain 3-methyl-1H-indol-6-ol as brown crystals.

MS: 146.0 (M–H)$^-$.

d] 3-Methyl-6-[4-methyl-2-(4-trifluoromethyl-phenyl)-thiazol-5-ylmethoxy]-1H-indole In analogy to the procedure described in example 27 e], 3-methyl-1H-indol-6-ol was reacted with 5-chloromethyl-4-methyl-2-(4-trifluoromethyl-phenyl)-thiazole [PCT Int. Appl. (2002), WO 0292590 A1] in the presence of cesium carbonate to give 3-methyl-6-[4-methyl-2-(4-trifluoromethyl-phenyl)-thiazol-5-ylmethoxy]-1H-indole as light brown crystals.

MS: 401.1 (M–H)$^-$.

e] {3-Methyl-6-[4-methyl-2-(4-trifluoromethyl-phenyl)-thiazol-5-ylmethoxy]-indol-1-yl}-acetic acid tert-butyl ester In analogy to the procedure described in example 27 f], 3-methyl-6-[4-methyl-2-(4-trifluoromethyl-phenyl)-thiazol-5-ylmethoxy]-1H-indole was reacted with tert-butyl bromoacetate in the presence of sodium hydride to obtain {3-methyl-6-[4-methyl-2-(4-trifluoromethyl-phenyl)-thiazol-5-ylmethoxy]-indol-1-yl}-acetic acid tert-butyl ester as brown oil.

MS: 517.3 (M+H)$^+$.

f] {3-Methyl-6-[4-methyl-2-(4-trifluoromethyl-phenyl)-thiazol-5-ylmethoxy]-indol-1-yl}-acetic acid In analogy to the procedure described in example 2 c], {3-methyl-6-[4-methyl-2-(4-trifluoromethyl-phenyl)-thiazol-5-ylmethoxy]-indol-1-yl}-acetic acid tert-butyl ester was treated with LiOH to obtain {3-methyl-6-[4-methyl-2-(4-trifluoromethyl-phenyl)-thiazol-5-ylmethoxy]-indol-1-yl}-acetic acid as off-white solid.

MS: 459.3 (M–H)$^-$.

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Gelatine | 150.0 mg |
| Phenol | 4.7 mg |

-continued

| | |
|---|---|
| Sodium carbonate | to obtain a final pH of 7 |
| Water for injection solutions | ad 1.0 ml |

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavoring additives and filled into sachets.

What is claimed is:

1. A compound of the formula

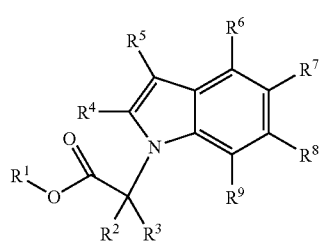

wherein $R^1$ is hydrogen or $C_{1-7}$-alkyl;
$R^2$ and $R^3$ independently from each other are hydrogen, $C_{1-7}$-alkyl or $C_{1-7}$-alkoxy,
$R^4$ and $R^5$ independently from each other are hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano;
$R^6$, $R^7$, $R^8$ and $R^9$ independently from each other are hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano;
and one of $R^6$, $R^7$ and $R^8$ is

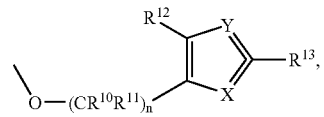

wherein
X is N and Y is S; or
X is S and Y is N;
$R^{10}$ is hydrogen, $C_{1-7}$-alkyl, $C_{3-7}$-cycloalkyl or fluoro-$C_{1-7}$-alkyl;
$R^{11}$ is hydrogen, $C_{1-7}$-alkyl or $C_{1-7}$-alkoxy-$C_{1-7}$-alkyl;
$R^{12}$ is hydrogen, $C_{1-7}$-alkyl, $C_{3-7}$-cycloalkyl or fluoro-$C_{1-7}$-alkyl;
$R^{13}$ is aryl or heteroaryl;
n is 1, 2 or 3; and
all enantiomers and pharmaceutically acceptable salts and/or esters thereof.

2. The compound of claim 1 of the formula

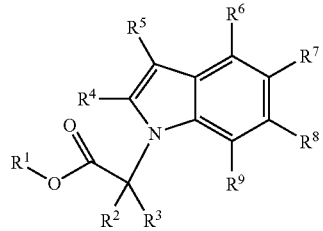

wherein
$R^1$ is hydrogen or $C_{1-7}$-alkyl;
$R^2$ and $R^3$ independently from each other are hydrogen, $C_{1-7}$-alkyl or $C_{1-7}$-alkoxy;
$R^4$ and $R^5$ independently from each other are hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano;
$R^6$, $R^7$, $R^8$ and $R^9$ independently from each other are hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano;
and one of $R^6$, $R^7$ and $R^8$ is

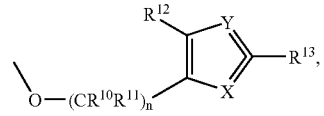

wherein
X is N and Y is S; or
X is S and Y is N;
R$^{10}$ is hydrogen, C$_{1-7}$-alkyl, C$_{3-7}$-cycloalkyl or fluoro-C$_{1-7}$-alkyl;
R$^{11}$ is hydrogen, C$_{1-7}$-alkyl or C$_{1-7}$-alkoxy-C$_{1-7}$-alkyl;
R$^{12}$ is hydrogen, C$_{1-7}$-alkyl, C$_{3-7}$-cycloalkyl or fluoro-C$_{1-7}$-alkyl;
R$^{13}$ is aryl or heteroaryl;
n is 1, 2 or 3; and
all enantiomers and pharmaceutically acceptable salts and/or esters thereof, provided that compounds of formula I are excluded, wherein
one of R$^7$ or R$^8$ is

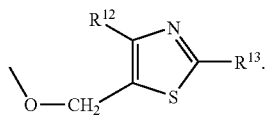

3. The compound of claim 1, wherein {5-[4-methyl-2-(4-trifluoromethyl-phenyl)-thiazol-5-yl-methoxy]-indol-1-yl}-acetic acid is excluded.

4. The compound of claim 2 having the formula

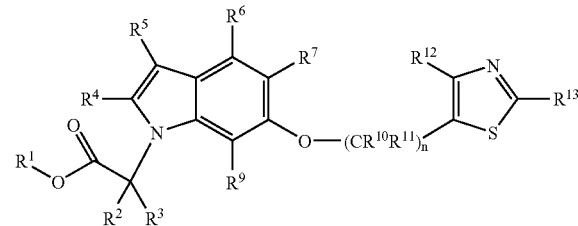

I-A wherein
R$^1$, R$^2$, R$^3$, R$^4$, R$^5$, R$^6$, R$^7$, R$^9$, R$^{10}$, R$^{11}$, R$^{12}$, R$^{13}$ and and all enantiomers and pharmaceutically acceptable salts and/or esters thereof.

5. The compound of claim 4, wherein R$^6$, R$^7$ and R$^9$ are hydrogen.

6. The compound of claim 2 having the formula

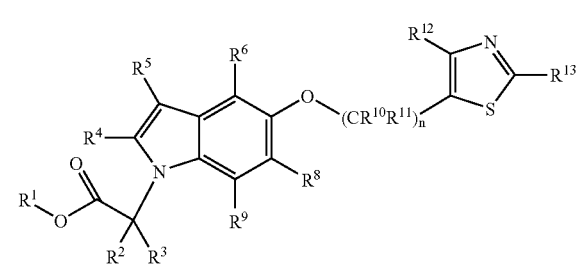

I-B wherein
R$^1$, R$^2$, R$^3$, R$^4$, R$^5$, R$^6$, R$^8$, R$^9$, R$^{10}$, R$^{11}$, R$^{12}$, R$^{13}$ and and all enantiomers and pharmaceutically acceptable salts and/or esters thereof.

7. The compound of claim 6, wherein R$^6$, R$^8$ and R$^9$ are hydrogen.

8. The compound of claim 2 having the formula

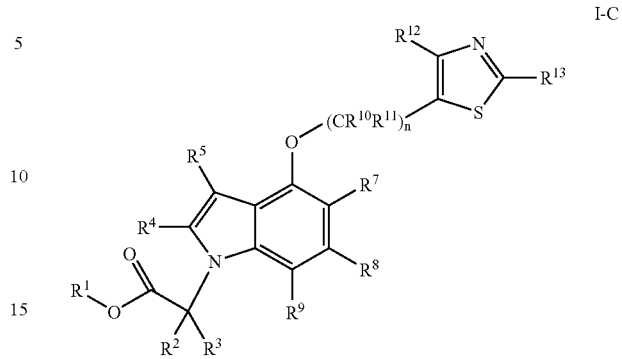

I-C wherein
R$^1$, R$^2$, R$^3$, R$^4$, R$^5$, R$^7$, R$^8$, R$^9$, R$^{10}$, R$^{11}$, R$^{12}$, R$^{13}$ and and all enantiomers and pharmaceutically acceptable salts and/or esters thereof.

9. The compound of claim 8, wherein R$^7$, R$^8$ and R$^9$ are hydrogen.

10. The compound of claim 2 having the formula

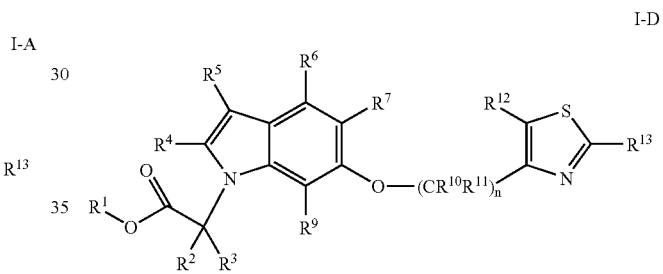

I-D wherein
R$^1$, R$^2$, R$^3$, R$^4$, R$^5$, R$^6$, R$^7$, R$^9$, R$^{10}$, R$^{11}$, R$^{12}$, R$^{13}$ and and all enantiomers and pharmaceutically acceptable salts and/or esters thereof.

11. The compound of claim 10, wherein R$^6$, R$^7$ and R$^9$ are hydrogen.

12. The compound of claim 2, wherein R$^1$ is hydrogen.

13. The compound of claim 2, wherein R$^2$ and R$^3$ independently from each other are hydrogen or methyl.

14. The compound of claim 2, wherein R$^4$ is hydrogen.

15. The compound of claim 2, wherein R$^5$ is hydrogen, C$_{1-7}$-alkyl or halogen.

16. The compound of claim 2, wherein R$^{10}$ is hydrogen, C$_{1-7}$-alkyl or C$_{3-7}$-cycloalkyl.

17. The compound of claim 16, wherein R$^{10}$ is C$_{1-7}$-alkyl or C$_{3-7}$-cycloalkyl.

18. The compound of claim 2, wherein R$^{11}$ is hydrogen.

19. The compound of claim 2, wherein n is 2.

20. The compound of claim 2, wherein R$^{12}$ is hydrogen or C$_{1-7}$-alkyl.

21. The compound of claim 20, wherein R$^{12}$ is methyl.

22. The compound of claim 2, wherein R$^{13}$ is unsubstituted phenyl or phenyl substituted with one to three groups selected from C$_{1-7}$-alkyl, C$_{1-7}$-alkoxy, halogen, fluoro-C$_{1-7}$-alkyl and cyano.

23. The compound of claim 2, wherein R$^{13}$ is phenyl substituted with halogen or fluoro-C$_{1-7}$-alkyl.

24. The compound of claim 23, wherein $R^{13}$ is 4-trifluoromethylphenyl.

25. A compound of claim 1, selected from the group consisting of
{3-ethyl-5-[4-methyl-2-(4-trifluoromethyl-phenyl)-thiazol-5-ylmethoxy]-indol-1-yl}-acetic acid,
[rac]-(6-{1-[4-methyl-2-(4-trifluoromethyl-phenyl)-thiazol-5-yl]-ethoxy}-indol-1-yl-acetic acid,
(6-{2-[4-methyl-2-(4-trifluoromethyl-phenyl)-thiazol-5-yl]-ethoxy}-indol-1-yl)-acetic acid,
{6-[2-(3-fluoro-4-trifluoromethyl-phenyl)-4-methyl-thiazol-5-ylmethoxy]-indol-1-yl}-acetic acid tert-butyl ester, and
(R)-(6-{1-[4-methyl-2-(4-trifluoromethyl-phenyl)-thiazol-5-yl]-ethoxy}-indol-1-yl) -acetic acid.

26. A compound of claim 2, selected from the group consisting of
{4-[4-methyl-2-(4-trifluoromethyl-phenyl)-thiazol-5-ylmethoxy]-indol-1-yl}-acetic acid,
[rac]-(6-{1-[4-methyl-2-(4-trifluoromethyl-phenyl)-thiazol-5-yl]-ethoxy}-indol-1-yl-acetic acid,
[rac]-(4-{2-methyl-1-[4-methyl-2-(4-trifluoromethyl-phenyl)-thiazol-5-yl]-propoxy}-indol-1-yl)-acetic acid,
[rac]-2-{4-[4-methyl-2-(4-trifluoromethyl-phenyl)-thiazol-5-ylmethoxy]-indol-1-yl}-propionic acid,
(4-{2-[4-methyl-2-(4-trifluoromethyl-phenyl)-thiazol-5-yl]-ethoxy}-indol-1-yl)-acetic acid,
{6-[2-(4-trifluoromethyl-phenyl)-thiazol-5-ylmethoxy]-indol-1-yl}-acetic acid,
(6-{2-[4-methyl-2-(4-trifluoromethyl-phenyl)-thiazol-5-yl]-ethoxy}-indol-1-yl)-acetic acid,
(4-{3-[4-methyl-2-(4-trifluoromethyl-phenyl)-thiazol-5-yl]-propoxy}-indol-1-yl)-acetic acid,
[rac]-(6-{2-methyl-1-[4-methyl-2-(4-trifluoromethyl-phenyl)-thiazol-5-yl]-propoxy}-indol-1-yl)-acetic acid,
(6-{3-[4-methyl-2-(4-trifluoromethyl-phenyl)-thiazol-5-yl]-propoxy}-indol-1-yl)-acetic acid,
(S)-(6-{1-[4-methyl-2-(4-trifluoromethyl-phenyl)-thiazol-5-yl]-ethoxy}-indol-1-yl) -acetic acid,
(R)-(6-{1-[4-methyl-2-(4-trifluoromethyl-phenyl)-thiazol-5-yl]-ethoxy}-indol-1-yl) -acetic acid,
[6-(5-methyl-2-phenyl-thiazol-4-ylmethoxy)-indol-1-yl]-acetic acid,
[rac]-(5-{1-[4-methyl-2-(4-trifluoromethyl-phenyl)-thiazol-5-yl]-ethoxy}-indol-1-yl-acetic acid,
(6-{2-[5-methyl-2-(4-trifluoromethyl-phenyl)-thiazol-4-yl]-ethoxy}-indol-1-yl)-acetic acid,
(6-{2-[2-(4-trifluoromethyl-phenyl)-thiazol-4-yl]-ethoxy}-indol-1-yl)-acetic acid,
(3-chloro-6-{2-[4-methyl-2-(4-trifluoromethyl-phenyl)-thiazol-5-yl]-ethoxy}-indol-1-yl)- acetic acid,
(6-{2-[4-methyl-2-(3-trifluoromethyl-phenyl)-thiazol-5-yl]-ethoxy}-indol-1-yl)-acetic acid,
{6-[2-(4-methyl-2-phenyl-thiazol-5-yl)-ethoxy]-indol-1-yl}-acetic acid,
(3-methyl-6-{2-[4-methyl-2-(4-trifluoromethyl-phenyl)-thiazol-5-yl]-ethoxy}-indol-1-yl)-acetic acid,
(6-{2-[4-methyl-2-(4-trifluoromethyl-phenyl)-thiazol-5-yl]-ethoxy}-3-propyl-indol-1-yl)-acetic acid,
{6-[5-methyl-2-(4-trifluoromethyl-phenyl)-thiazol-4-ylmethoxy]-indol-1-yl}-acetic acid,
(6-{2-[4-methyl-2-(4-trifluoromethoxy-phenyl)-thiazol-5-yl]-ethoxy}-indol-1-yl)-acetic acid,
[rac]-(6-{4-hydroxy-1-[4-methyl-2-(4-trifluoromethyl-phenyl)-thiazol-5-yl]-butoxy}-indol-1-yl)-acetic acid, and
{6-[2-(5-methyl-2-phenyl-thiazol-4-yl)-ethoxy]-indol-1-yl}-acetic acid.

27. A compound of claim 2, selected from the group consisting of
(6-{2-[4-methyl-2-(4-trifluoromethyl-phenyl)-thiazol-5-yl]-ethoxy}-indol-1-yl)-acetic acid,
(6-{3-[4-methyl-2-(4-trifluoromethyl-phenyl)-thiazol-5-yl]-propoxy}-indol-1-yl)-acetic acid,
(R)-(6-{1-[4-methyl-2-(4-trifluoromethyl-phenyl)-thiazol-5-yl]-ethoxy}-indol-1-yl) -acetic acid, and
[rac]-(5-{1-[4-methyl-2-(4-trifluoromethyl-phenyl)-thiazol-5-yl]-ethoxy}-indol-1-yl)-acetic acid.

28. A process for the manufacture of a compound of claim 1, which process comprises a) reacting a compound of formula

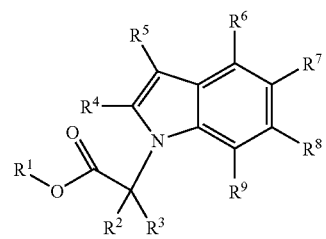

II wherein $R^1$ is $C_{1-7}$-alkyl, $R^2$, $R^3$, $R^4$ and $R^5$ are as defined as in claim 1 and $R^6$, $R^9$ are selected from hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl, and cyano with the proviso that one of $R^6$, $R^7$ or $R^8$ is —OH, with a compound of formula

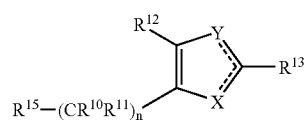

III wherein X, Y, $R^{10}$, $R^{11}$, $R^{12}$, $R^{13}$ and n are as defined in claim 1 and $R^{15}$ is —OH, —Cl, —Br, —I or another leaving group, to obtain a compound of formula

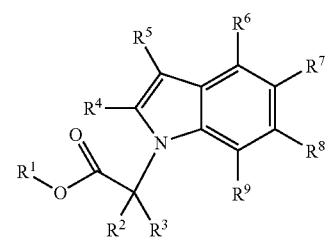

I wherein $R^1$ is $C_{1-7}$-alkyl and $R^2$ to $R^9$ are as defined in claim 1, and optionally hydrolysing the ester group to obtain a compound of formula I, wherein $R^1$ is hydrogen;

or, alternatively, b) reacting a compound of formula

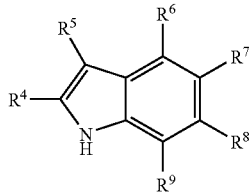
IV wherein $R^4$ to $R^9$ are as defined as in claim 1, with a compound of formula

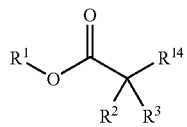
V wherein $R^1$ is $C_{1-7}$-alkyl, $R^2$ and $R^3$ are as defined in claim 1 and $R^{14}$ is halogen, triflate or another leaving group, to obtain a compound of formula

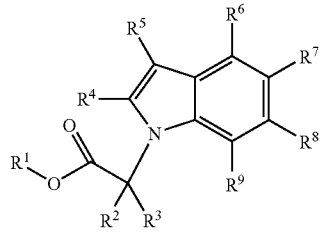
I wherein $R^1$ is $C_{1-7}$-alkyl and $R^2$ to $R^9$ are as defined in claim 1, and optionally hydrolysing the ester group to obtain a compound of formula I, wherein $R^1$ is hydrogen.

29. A pharmaceutical composition comprising a compound of the formula

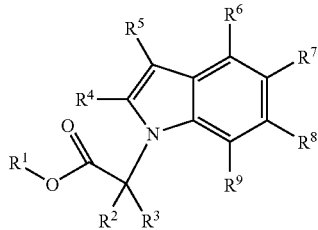
I wherein $R^1$ is hydrogen or $C_{1-7}$-alkyl;

$R^2$ and $R^3$ independently from each other are hydrogen, $C_{1-7}$-alkyl or $C_{1-7}$-alkoxy, $R^4$ and $R^5$ independently from each other are hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano;

$R^6$, $R^7$, $R^8$ and $R^9$ independently from each other are hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano;

and one of $R^6$, $R^7$ and $R^8$ is

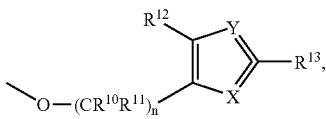

wherein

X is N and Y is S; or

X is S and Y is N;

$R^{10}$ is hydrogen, $C_{1-7}$-alkyl, $C_{3-7}$-cycloalkyl or fluoro-$C_{1-7}$-alkyl;

$R^{11}$ is hydrogen, $C_{1-7}$-alkyl or $C_{1-7}$-alkoxy-$C_{1-7}$-alkyl;

$R^{12}$ is hydrogen, $C_{1-7}$-alkyl, $C_{3-7}$-cycloalkyl or fluoro-$C_{1-7}$-alkyl;

$R^{13}$ is aryl or heteroaryl;

n is 1, 2 or 3; and all enantiomers and pharmaceutically acceptable salts and/or esters thereof; and a pharmaceutically acceptable carrier or excipient.

* * * * *

UNITED STATES PATENT AND TRADEMARK OFFICE
CERTIFICATE OF CORRECTION

| | |
|---|---|
| PATENT NO. | : 7,235,572 B2 |
| APPLICATION NO. | : 10/878473 |
| DATED | : June 26, 2007 |
| INVENTOR(S) | : Jean Ackermann et al. |

Page 1 of 1

It is certified that error appears in the above-identified patent and that said Letters Patent is hereby corrected as shown below:

Title Page, (73) Assignee: delete "Hoffman-La Roche Inc., Nutley, NJ (US)"
and insert -- Hoffmann-La Roche Inc., Nutley, NJ (US) --

Column 61, Claim 4, line 41, delete "and and" and insert
-- and n are as defined in claim 2 and --

Column 61, Claim 6, line 63, delete "and and" and insert
-- and n are as defined in claim 2 and --

Column 62, Claim 8, line 20, delete "and and" and insert
-- and n are as defined in claim 1 and --

Column 62, Claim 10, line 41, delete "and and" and insert
-- and n are as defined in claim 1 and --

Column 64, Claim 28, line 32, after " and $R^6$," insert
-- $R^7$, $R^8$ and --

Signed and Sealed this

Twenty-eighth Day of August, 2007

JON W. DUDAS
*Director of the United States Patent and Trademark Office*